US008951470B2

(12) United States Patent
Oonuma

(10) Patent No.: US 8,951,470 B2
(45) Date of Patent: Feb. 10, 2015

(54) AUTOANALYZER AND PROBE ELEVATING METHOD

(75) Inventor: Takehiko Oonuma, Sakura (JP)

(73) Assignees: Kabushiki Kaisha Toshiba, Tokyo (JP); Toshiba Medical Systems Corporation, Otawara-shi (JP)

(*) Notice: Subject to any disclaimer, the term of this patent is extended or adjusted under 35 U.S.C. 154(b) by 401 days.

(21) Appl. No.: 12/179,620

(22) Filed: Jul. 25, 2008

(65) Prior Publication Data
US 2009/0000401 A1 Jan. 1, 2009

Related U.S. Application Data

(63) Continuation of application No. PCT/JP2007/051198, filed on Jan. 25, 2007.

(30) Foreign Application Priority Data

Jan. 27, 2006 (JP) .................. 2006-018646

(51) Int. Cl.
C12Q 1/68 (2006.01)
G01N 35/10 (2006.01)
G01N 35/00 (2006.01)

(52) U.S. Cl.
CPC ........ G01N 35/1011 (2013.01); G01N 35/1009 (2013.01); G01N 35/1016 (2013.01); G01N 2035/00277 (2013.01); G01N 2035/1025 (2013.01)
USPC .......................................................... 422/50

(58) Field of Classification Search
CPC ................ G01N 35/1011; G01N 35/1009
USPC .......................................................... 422/50
See application file for complete search history.

(56) References Cited

U.S. PATENT DOCUMENTS 6,270,726 B1 * 8/2001 Tyberg et al. ................. 422/100
2002/0064481 A1 5/2002 Ishizawa et al.

FOREIGN PATENT DOCUMENTS

JP 63-169565 7/1988
JP 5-99933 4/1993
JP 10-153601 A 6/1998

(Continued)

OTHER PUBLICATIONS

Japanese Office Action issued Nov. 29, 2011 in patent application No. 2007-015198 with English translation.

(Continued)

Primary Examiner — Jonathan Hurst
(74) Attorney, Agent, or Firm — Oblon, Spivak, McClelland, Maier & Neustadt, L.L.P.

(57) ABSTRACT

An autoanalyzer includes a measurement unit which measures a reaction liquid produced by an interaction between a reagent and an examined sample contained in a reaction container, a sample probe which sucks the examined sample from a sample container and discharges the examined sample to the reaction container, a probe elevating arm which elevates the sample probe with respect to the sample container, and a control unit which controls the probe elevating arm so that a speed at which the sample probe enters a liquid surface of the examined sample to perform an n-th suction operation (n≥2) of the examined sample is slower than a speed at which the sample probe enters the liquid surface of the examined sample to perform a first suction operation of the examined sample.

5 Claims, 14 Drawing Sheets

(56) References Cited

FOREIGN PATENT DOCUMENTS

| JP | 11-271322 A | 10/1999 |
|----|----|----|
| JP | 2000-171470 A | 6/2000 |
| JP | 2002-40032 A | 2/2002 |
| JP | 2002-162401 | 6/2002 |
| JP | 2002-303633 | 10/2002 |

OTHER PUBLICATIONS

European Search Report issued Oct. 14, 2010 in European Application No. 07 707 430.0.

* cited by examiner

AUTOANALYZER AND PROBE ELEVATING METHOD

CROSS REFERENCE TO RELATED APPLICATIONS

This is a Continuation Application of PCT Application No. PCT/JP2007/051198, filed Jan. 25, 2007, which was published under PCT Article 21(2) in Japanese.

This application is based upon and claims the benefit of priority from prior Japanese Patent Application No. 2006-018646, filed Jan. 27, 2006, the entire contents of which are incorporated herein by reference.

BACKGROUND OF THE INVENTION

1. Field of the Invention

The present invention relates to an autoanalyzer for analyzing components contained in a liquid and a dispensing method thereof, and more particularly, to an autoanalyzer for automatically measuring components contained in a body fluid by dispensing the body fluid such as human blood or urine and a probe elevating method thereof.

2. Description of the Related Art

An autoanalyzer measures a light transmitting amount to check a variation in a color tone and the like generated during a reaction of a mixed liquid produced by mixing an examined sample dispensed into a reaction container with a reagent corresponding to a measurement item such as biochemistry or immunity, thereby measuring a ferment activation or a density for each examined material in the examined sample.

The autoanalyzer measures a measurement item selected in accordance with an examination among a plurality of measurement items, which can be measured in accordance with an analysis condition setting for each examined sample. Then, the reagent corresponding to the measurement item and the examined sample are dispensed into the reaction container via a sample/reagent dispensing probe, the examined sample and the reagent dispensed into the reaction container are stirred by a stirrer to be mixed, and then the mixed liquid is measured by a photometric portion. Additionally, the sample/reagent dispensing probe contacting with the examined sample and the reagent, the stirrer, and the reaction container contacting with the mixed liquid are cleaned and used again for the next measurement.

In the recent autoanalyzer, respective analysis units are interlocked with each other and are operated at a high speed so that the measurement operation of the examined sample is carried out in a predetermined short analysis cycle and a plurality of measurement items and a plurality of examined samples are processed at a high speed.

Then, in an examined sample dispensing process, for 1 analysis cycle, the sample dispensing probe sucks the examined sample in a sample container via a pressure transmission medium such as water inserted in the sample dispensing probe, a tube between the sample dispensing probes, and a sample dispensing pump for performing a suction/discharge operation, and a sample dispensing arm horizontally moves and elevates the sample dispensing probe so as to discharge the sucked examined sample into the reaction container.

In the suction operation of the first dispensing operation upon performing the examined sample dispensing process a plurality of times, first, the sample dispensing probe moves horizontally to a position above the sample container and air is sucked into the sample dispensing probe.

Subsequently, after the sample dispensing probe moves horizontally to the position above the sample container, air is sucked. Subsequently, the sample dispensing probe moves down to the examined sample in the sample container, and a liquid surface of the examined sample is detected by a detector when the sample dispensing probe enters the examined sample in the sample container. Subsequently, the sample dispensing probe stops at a suction position slightly deeper than the detection position so as to suck the examined sample.

After the sample dispensing probe moves down, the sample dispensing probe sucks a dummy examined sample and a measurement examined sample from the sample container for the first dispensing operation, and discharges only the first measurement examined sample into the reaction container.

In the n-th dispensing operation (n≥2), the sample dispensing probe operates at the same timing as that of the first sample dispensing process. The sample dispensing probe sucks only the measurement examined sample for the n-th dispensing operation, and discharges only the n-th measurement examined sample into the reaction container. After all of the measurement examined sample dispensing processes ends, the air and the dummy examined sample sucked during the first dispensing operation are discharged and the inside and outside portions of the sample dispensing probe are cleaned after the discharge.

An air layer and a dummy examined sample layer are formed inside the sample dispensing probe during the suction operation of the first dispensing operation so as to isolate each measurement examined sample sucked into the sample dispensing probe from the pressure transmission medium and to prevent the measurement examined sample from diluting due to a mix with the dispersed pressure transmission medium and the like, thereby preventing a deterioration in precision upon dispensing the examined sample (for example, see JP-A-2002-162401).

However, in the suction operation of the dispensing operation, since the sample dispensing probe enters the examined sample in the sample container at a high speed, when the number of the dispensing operations of the same examined sample increases, the number of shocks upon stopping at the suction position increases, and the pressure transmission medium mixes with the air layer formed inside the sample dispensing probe to thereby diffuse a part of the air. As a result, a problem arises in that the air layer is thinned, and a problem arises in that the pressure transmission medium is mixed with the dummy examined sample formed during the first dispensing operation to thereby be diluted because of the thinned air layer. Due to such problems, when the number of the dispensing operations of the same examined sample increases, a problem arises in that the precision upon dispensing the examined sample deteriorates.

BRIEF SUMMARY OF THE INVENTION

An object of the invention is to provide an autoanalyzer and a method of elevating a probe for dispensing an examined sample with high precision.

According to the invention, there is provided an autoanalyzer including: a measurement unit which measures a reaction liquid produced by an interaction between a reagent and an examined sample contained in a reaction container; a sample probe which sucks the examined sample from a sample container and discharges the examined sample to the reaction container; a probe elevating mechanism which elevates the sample probe with respect to the sample container; and a control unit which controls the probe elevating mechanism so that a speed at which the sample probe enters a liquid surface of the examined sample to perform an n-th suction operation (n≥2) of the examined sample is slower than a speed at which the sample probe enters the liquid surface of the examined sample to perform a first suction operation of the examined sample.

DETAILED DESCRIPTION OF THE INVENTION

Hereinafter, an autoanalyzer according to an embodiment of the invention will be described with reference to FIGS. 1 to 13.

Figure 1:
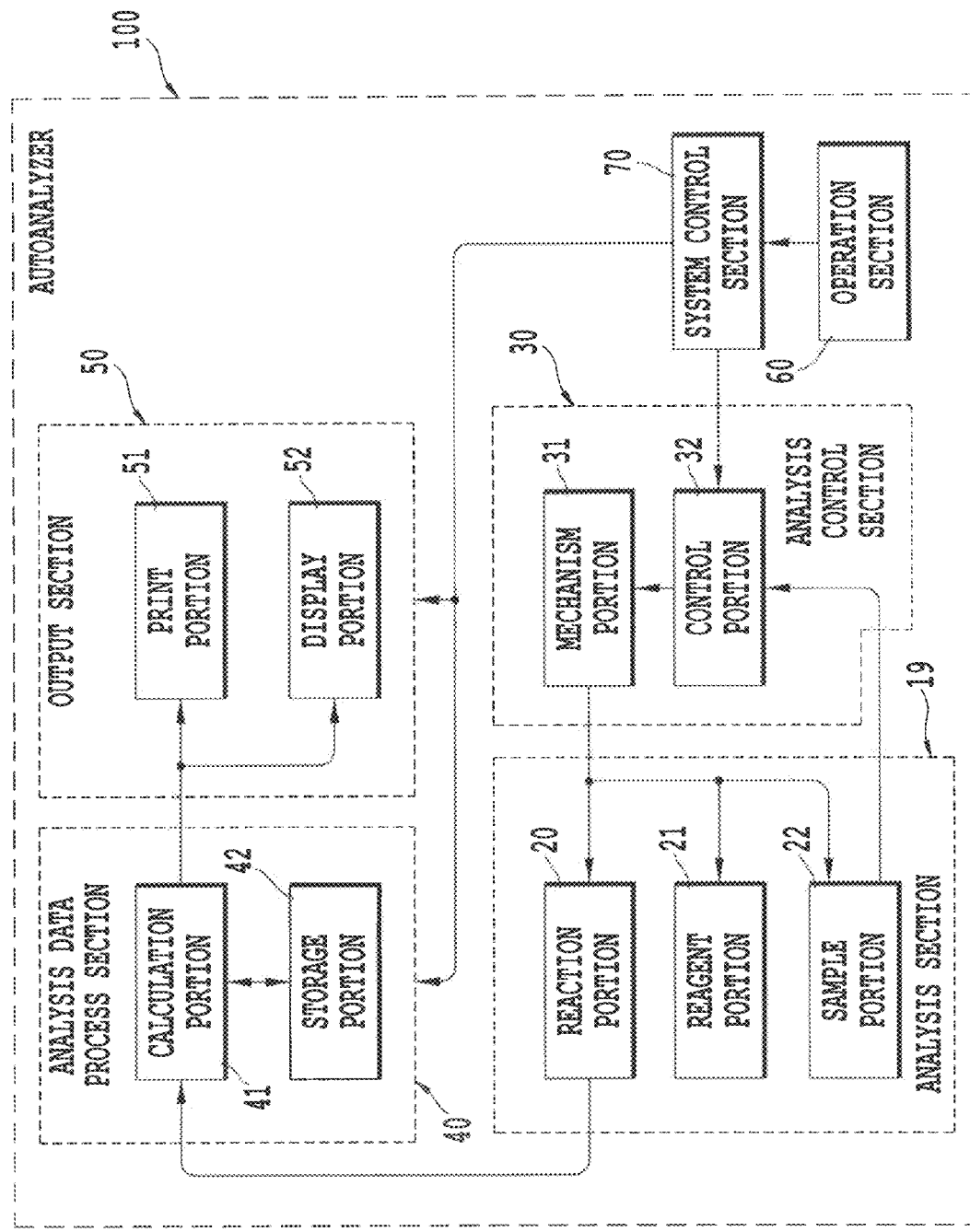
FIG. 1 is a view showing a configuration of an autoanalyzer according to an embodiment of the invention.

FIG. 1 is a block diagram showing a configuration of the autoanalyzer according to the embodiment of the invention. An autoanalyzer 100 includes an analysis section 19 which measures a measurement item selectively input for each examined sample or calibrator of various measurement items; an analysis control section 30 which controls a measurement operation of the analysis section 19; an analysis data process section 40 which processes analysis signals output from the analysis section 19 to generate analysis data; an output section 50 which outputs analysis data from the analysis data process section 40; an operation section 60 which inputs various command signals, a measurement item selection input for each examined sample or an analysis condition setting for each measurement item; and a system control section 70 which generally controls the above-described units.

The analysis section 19 includes a sample portion 20 which has an analysis unit and the like for handing samples such as an examined sample and a calibrator for each measurement item; a reagent portion 21 which has an analysis unit and the like for handing reagents chemically reacted with components of the measurement item of the sample; and a reaction portion 22 which has an analysis unit and the like for measuring mixed liquid of the sample and the reagents. Then, calibrator signals or analysis signals generated upon measuring the calibrator or the examined sample are output from the reaction portion 22 to the analysis data process section 40.

The analysis control section 30 includes a mechanism portion 31 which has mechanisms for driving the analysis unit and the like of the analysis section 19 and a control portion 32 which controls the mechanisms of the mechanism portion 31.

The analysis data process section 40 includes a calculation portion 41 which performs a calibration table creation for each measurement item, an analysis data calculation for each measurement item of each examined sample, and the like on the basis of the calibrator signals or the analysis signals output from the reaction portion 22 of the analysis section 19, and a storage portion 42 which stores the calculated analysis data or the calibration table created by the calculation portion 41.

The calculation portion 41 creates the calibration table for each measurement item on the basis of the calibrator signals for each measurement item output from the reaction portion 22 of the analysis section 19, outputs the calibration table to the output section 50, and then stores the calibration table in the storage portion 42. In addition, after the calculation portion reads out the calibration table for the measurement item from the storage portion 42 in response to the analysis signals for each measurement item of each examined sample output from the reaction portion 22 of the analysis section 19, the calculation portion calculates analysis data using the calibration table, outputs the analysis data to the output section 50, and then stores the analysis data in the storage portion 42.

The storage portion 42 includes a hard disk and the like, and stores the calibration table, the analysis data, and the like output from the calculation portion 41 for each examined sample.

The output section 50 includes a print portion 51 which prints the calibration table, the analysis data, and the like output from the calculation portion 41 of the analysis data process section 40, and a display portion 52 which performs a display output.

The print portion 51 includes a printer and the like, and prints the calibration table, the analysis data, and the like output from the calculation portion 41 of the analysis data process portion 40 in accordance with a predetermined format on a printer sheet and the like.

The display portion 52 includes a monitor such as a CRT or a liquid crystal panel, and displays the calibration table or the analysis data output from the calculation portion 41 of the analysis data process section 40, an examined body information input screen for inputting an ID, a name, and the like of an examined body, an analysis condition setting screen for setting an analysis condition for each measurement item, a measurement item setting screen for selectively setting the measurement item for each examined sample, and the like.

The operation section 60 includes input devices such as a keyboard, a mouse, a button, and a touch key panel, and performs various operations such as an analysis condition setting for each measurement item, an examined body information input such as an ID or a name of the examined body, a measurement item selection input for each examined sample, a calibration for each measurement item, and an examined sample measurement.

The system control section 70 includes a storage circuit and a CPU (not shown). After the system control section stores information such as a measurement item for each examined sample, examined body information, a measurement item analysis condition, an operator's command signal input from the operation section 60, on the basis of the information, the system control section controls an entire system control such as an analysis data calculation/output, a calibration table creation, and a control in which measurement operations of analysis units constituting the analysis section 19 are carried out at a predetermined cycle in accordance with a predetermined sequence.

Figure 2:
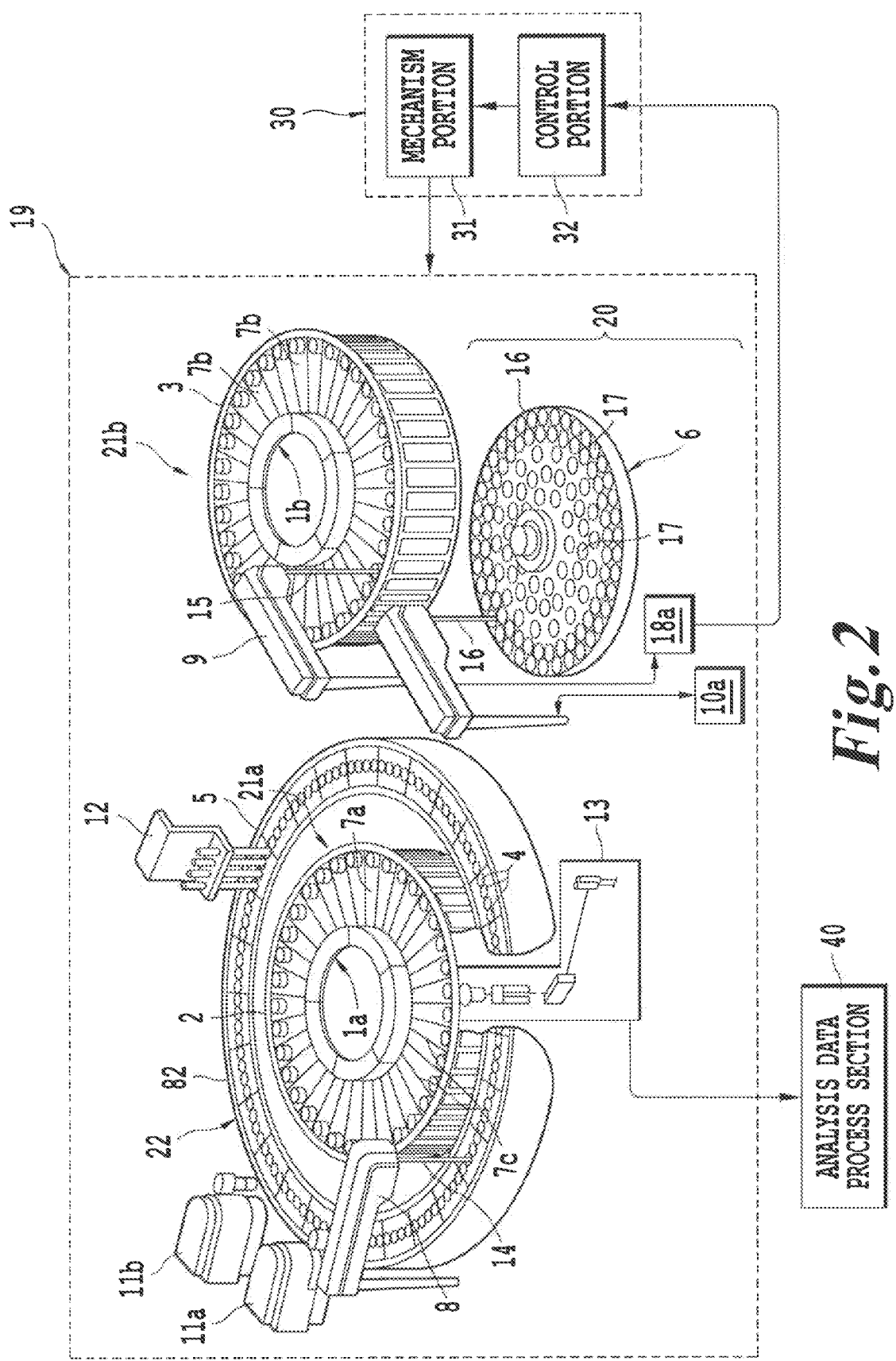
FIG. 2 is a perspective view showing a configuration of an analysis section according to the embodiment of the invention.

Next, a configuration of the analysis section 19 and the analysis control section 30 will be described in detail with reference to FIG. 2 or 3. FIG. 2 is a perspective view illustrating a configuration of the reaction portion 22, the reagent portion 21, and the sample portion 20 of the analysis section 19.

The sample portion 20 includes a sample container 17 which accommodates a sample such as an examined sample and a calibrator; a disk sampler 6 which rotatably supports the sample container 17 accommodating the sample; a sample dispensing probe 16 which sucks the sample from the sample container 17 of the disk sampler 6, discharges the sample at a discharge position of the reaction portion 22, and then is cleaned in a cleaning pool at a sample dispensing probe cleaning position (not shown) whenever ending a dispensing operation in which the same sample is sucked and discharged; and a sample dispensing arm 10 which supports the sample dispensing probe 16 so as to elevate and move horizontally in a calibrator suction position, an examined sample suction position, a sample discharge position of the reaction portion 22, and a sample dispensing probe cleaning position.

The sample dispensing arm 10 includes a probe elevating mechanism. The probe elevating mechanism is configured to adjust an elevation speed of the sample dispensing arm 10. The elevation speed of the sample dispensing arm 10 using the probe elevating mechanism is controlled by the control portion 32. In particular, a moving down speed control of the elevation speed of the sample dispensing arm 10 using the probe elevating mechanism will be described below in detail.

The sample portion 20 includes a detector 18a which detects a liquid surface of the sample when the sample dispensing probe 16 moves horizontally to the calibrator suction position or the examined sample suction position and then the front end portion of the moved down sample dispensing probe enters the sample of the sample container 17, and a detection signal of the detected sample is output to the control portion 32 of the analysis control section 30. Then, on the basis of the detection signal from the detector 18a, the sample dispensing probe 16 is controlled by the control portion 32 so as to be stopped at a suction position capable of sucking the sample at a predetermined depth from the liquid surface.

In addition, when a stop position of the sample dispensing probe 16 is too deep from the liquid surface of the examined sample, the sample is attached up to the upper outside portion of the sample dispensing probe 16 and the sample attached to the upper portion moves downward. Then, a problem arises in that a sample of a predetermined amount is discharged together with the sample moved downward upon discharging the sample. Additionally, a problem arises in that the upper outside portion of the sample dispensing probe 16 cannot be cleaned upon cleaning the sample dispensing probe in the cleaning pool at the sample dispensing probe cleaning position after the dispensing operation of the same sample. In order to prevent such problems, the sample dispensing probe is configured to be stopped, for example, at a suction position capable of sucking the sample at a predetermined depth of 2 mm or so from the liquid surface.

The reagent portion 21 includes a first reagent part 21a and a second reagent part 21b. The first reagent part 21a includes a reagent bottle 7a in which a first reagent selectively reacted with the sample is inserted, a reagent rack 1a which accommodates the reagent bottle 7a, and a reagent repository 2 which rotatably supports the reagent rack 1a. In addition, the second reagent part 21b includes a reagent bottle 7b in which a second reagent making a pair with the first reagent is inserted, a reagent rack 1b which accommodates the reagent bottle 7b, and a reagent repository 3 which rotatably supports the reagent rack 1b.

The first reagent part 21a includes a first reagent dispensing probe 14 which sucks the first reagent from the reagent bottle 7a stopped at a first reagent suction position, discharges the first reagent from a first reagent discharge position of the reaction portion 22, and then is cleaned in a cleaning pool at a first reagent dispensing probe cleaning position whenever ending a first reagent dispensing operation. In the same way, the second reagent part 21b includes a second reagent dispensing probe 15 which sucks the second reagent from the reagent bottle 7b stopped at a second reagent suction position, discharges the second reagent from a second reagent discharge position or the reaction portion 22, and then is cleaned in a cleaning pool at a second reagent cleaning position whenever ending a second reagent dispensing operation.

In addition, the first reagent part 21a includes a first reagent dispensing arm 8 which supports the first reagent dispensing probe 14 so as to elevate and move horizontally in the first reagent suction position, the first reagent discharge position of the reaction portion 22, and the first reagent dispensing probe cleaning position. In the same way, the second reagent part 21b includes a second reagent dispensing arm 9 which supports the second reagent dispensing probe 15 so as to elevate and move horizontally in the second reagent suction position, the second reagent discharge position of the reaction portion 22, and the second reagent dispensing probe cleaning position.

The reaction portion 22 includes a plurality of reaction containers 4 which are arranged on a circumference and receive the sample discharged from the sample dispensing probe 16 stopped at the sample discharge position, the first reagent discharged from the first reagent dispensing probe 14 stopped at the first reagent discharge position, and the second reagent discharged from the second reagent dispensing probe 15 stopped at the second reagent discharge position, and a reaction disk 5 which rotatably supports the reaction containers 4. Then, the reaction disk 5 rotates and stops in a counterclockwise direction, for example, at an analysis cycle of 4.5 sec, for example, the reaction disk rotates by an angle corresponding to one circumference and one reaction container 4 in 4 analysis cycle.

The reaction portion 22 includes a first stirring unit 11a which stirs mixed liquid of the first reagent and the sample in the reaction container 4 stopped at a first stirring position and supports a first stirrer so as to rotate and elevate between the first stirring position and a first stirrer cleaning position, the first stirrer being cleaned in a cleaning pool at the first stirrer cleaning position whenever ending a stirring operation of the mixed liquid.

In addition, the reaction portion 22 includes a second stirring unit 11b which stirs mixed liquid of the first reagent, the second reagent, and the sample in the reaction container 4 stopped at a second stirring position and supports a second stirrer so as to rotate and elevate between the second stirring position and a second stirrer cleaning position, the second stirrer being cleaned in a cleaning pool at the second stirrer cleaning position whenever ending a stirring operation of the mixed liquid.

In addition, the reaction portion 22 includes a photometric unit 13 which generates an analysis signal by irradiating light when the reaction container 4 having the mixed liquid after the first or second stirring operation passes a photometric position and by measuring a light absorption degree of a set wavelength on the basis of the transmitted light, and a cleaning unit 12 which sucks the mixed liquid, having been subjected to the measurement, in the reaction container 4 stopped at a cleaning and drying position and which elevatably supports a cleaning nozzle and a drying nozzle for respectively cleaning and drying the inside of the reaction container 4. Then, after the reaction container 4 is cleaned and dried by the cleaning unit 12, the reaction container is used again for the measurement.

Next, a configuration of the mechanism portion 31 of the analysis control section 30 will be described.

The mechanism portion 31 includes a rotation mechanism which rotates the disk sampler 6 of the sample portion 20, the reagent repository 2 of the first reagent part 21a, and the reagent repository 3 of the second reagent part 21b; a rotation mechanism which rotates the reaction disk 5 of the reaction portion 22; a rotation/elevation mechanism which rotates and elevates the sample dispensing arm 10 of the sample portion 20, the first reagent dispensing arm 8 of the first reagent part 21a, the second reagent dispensing arm 9 of the second reagent part 21b, and the first stirring unit 11a and the second stirring unit 11b of the reaction portion 22; and an elevation mechanism which elevates the cleaning unit 12 of the reaction portion 22.

In addition, the mechanism portion 31 includes a driving mechanism which drives a sample dispensing pump 10a for sucking the sample into the sample dispensing probe 16 or discharging the sample from the sample dispensing probe 16 via a pressure transmission medium such as water. Also, the mechanism portion includes a driving mechanism which drives a reagent pump for sucking or discharging the first reagent from the first reagent dispensing probe 14 and a driving mechanism which drives a reagent pump for sucking or discharging the second reagent from the second reagent dispensing probe 15. Also, the mechanism portion includes a driving mechanism which drives the first stirrer of the first stirring unit 11a to perform a stirring operation and a driving mechanism which drives the second stirrer of the second stirring unit 11b to perform a stirring operation. Also, the mechanism portion includes a driving mechanism which drives a cleaning pump for discharging or sucking a cleaning liquid from a cleaning nozzle of the cleaning unit 12. Also, the mechanism portion includes a driving mechanism which drives a drying pump for performing a suction operation in a drying nozzle of the cleaning unit 12.

The control portion 32 includes a control circuit which controls the respective mechanisms of the mechanism portion 31. On the basis of the signals from the control portion 32, the mechanism portion 31 operates the disk sampler 6, the reagent repository 2, the reagent repository 3, the reaction disk 5, the sample dispensing arm 10, the first reagent dispensing arm 8, the second reagent dispensing arm 9, the first stirring unit 11a, the second stirring unit 11b, the cleaning unit 12, the sample dispensing pump 10a, the reagent pump, the first stirrer, the second stirrer, the cleaning pump, the drying pump, and the like by an analysis cycle unit.

The control portion 32 controls the driving mechanism (for example, stepping motor) which drives the sample dispensing arm 10 of the mechanism portion 31 on the basis of the detection signal output from the detector 18a of the sample portion 20 so that the sample dispensing probe 16 stops at a sample suction position.

Figure 3:
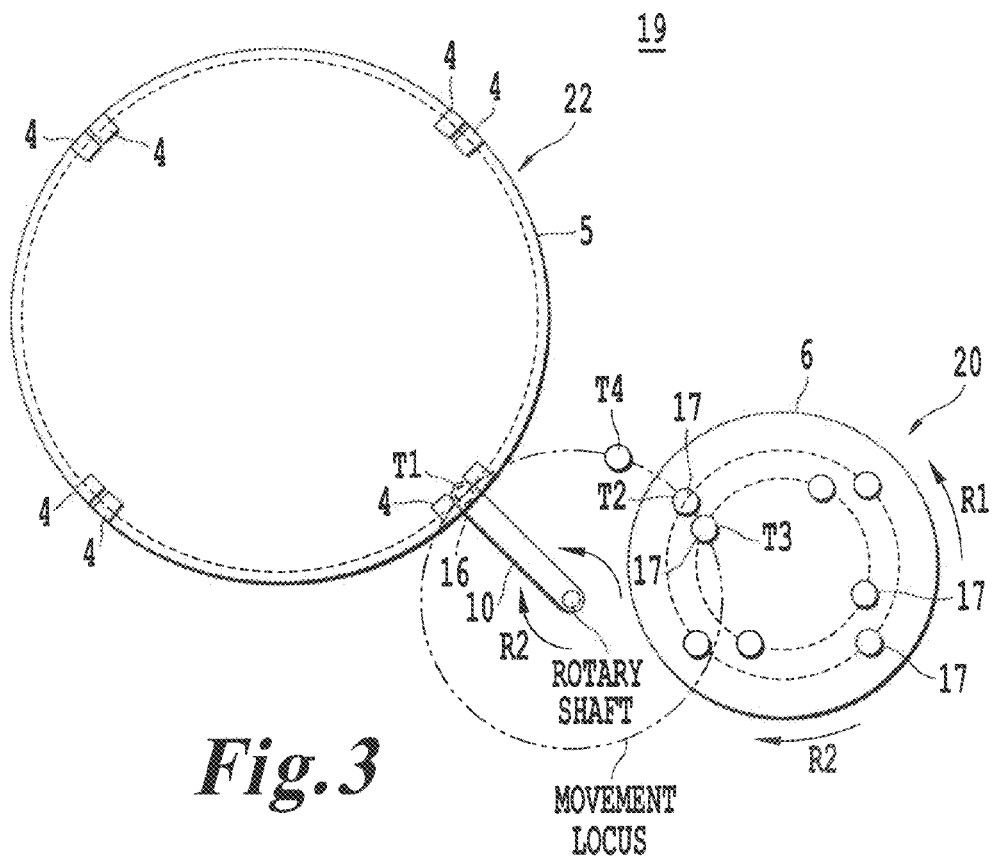
FIG. 3 is a view showing a part of a configuration of a sample portion and a reaction portion according to the embodiment of the invention.

FIG. 3 is a view showing a part of a configuration of the reaction portion 22 and the sample portion 20 of the analysis section 19 when viewed from the upside. The sample dispensing arm 10 rotates about a rotary shaft at the center in a direction indicated by the arrow R1 or R2 at a height corresponding to TDC so that the sample dispensing probe 16 at TDC moves horizontally along a movement locus indicated by a dashed line shown in FIG. 3.

On the movement locus of the sample dispensing probe 16, there are a sample discharge position T1 on the reaction portion 22, an examined sample suction position T2 and a calibrator suction position T3 on the sample portion 20, and a sample dispensing probe cleaning position T4 located among the sample discharge position T1, the examined sample suction position T2, and the calibrator suction position T3. Then, the sample dispensing probe 16 horizontally moves between the sample discharge position T1 and the examined sample suction position T2, between the sample discharge position T1 and the sample dispensing probe cleaning position T4, and among the sample dispensing probe cleaning position T4, the examined sample suction position T2, and the calibrator suction position T3.

That is, after the disk sampler 6 supporting the sample container 17 having the examined sample rotates in a direction indicated by R1 or R2, the sample dispensing probe 16 sucks the examined sample from the predetermined sample container 17 at a stop position below the examined sample suction position T2. Then, the sample dispensing probe moves horizontally to the sample discharge position T1 on the reaction portion 22, and discharges the sucked examined sample into the predetermined reaction container 4 at the stop position therebelow.

Subsequently, the sample dispensing probe is cleaned in the cleaning pool below the sample dispensing probe cleaning position T4 whenever ending the sample dispensing process in the sample container 17.

Figure 4:
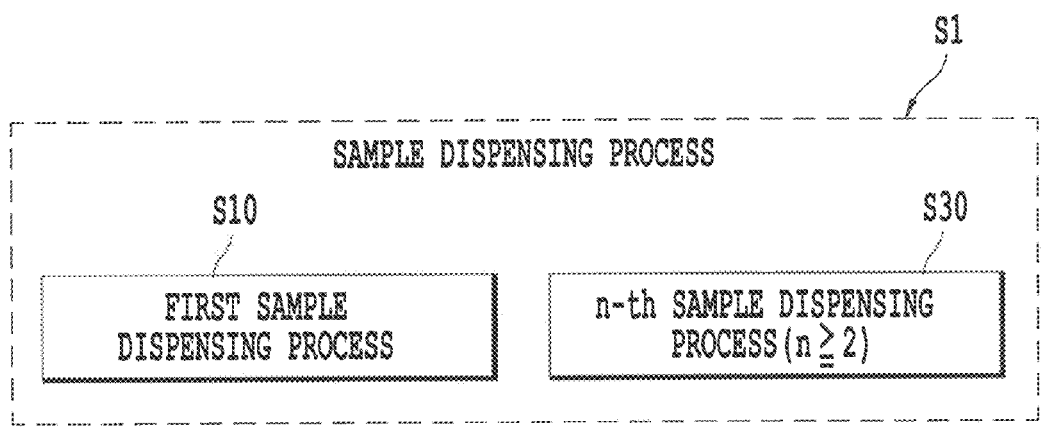
FIG. 4 is a view showing a configuration of a sample dispensing process according to the embodiment of the invention.

Next, the sample dispensing operation for dispensing the examined sample will be described in detail with reference to FIGS. 1 to 10B. FIG. 4 is a view showing a sample dispensing process for dispensing the examined sample.

A sample dispensing process S1 includes a first sample dispensing process S10 for dispensing the examined sample accommodated in the sample container 17 at the examined sample suction position T2 at the first time and an n-th sample dispensing process S30 for dispensing the examined sample at the n-th time (n≥2). Then, on the basis of the measurement command from the system control section 70, the control portion 32 of the analysis control section 30 controls the respective mechanisms of the mechanism portion 31 so as to drive the respective analysis units of the reaction disk 5, the sample dispensing arm 10, the sample dispensing pump 10a, and the like.

The first sample dispensing process S10 is carried out when the examined sample in the sample container 17 stopped at the examined sample suction position T2 is dispensed at the first time, and the n-th sample dispensing process S30 is carried out when the examined sample is dispensed at the n-th time that the same examined sample is dispersed for plural times in the same way as that of the first sample dispensing process S10. Then, each of the sample dispensing processes is carried out during 1 analysis cycle.

Figure 5:
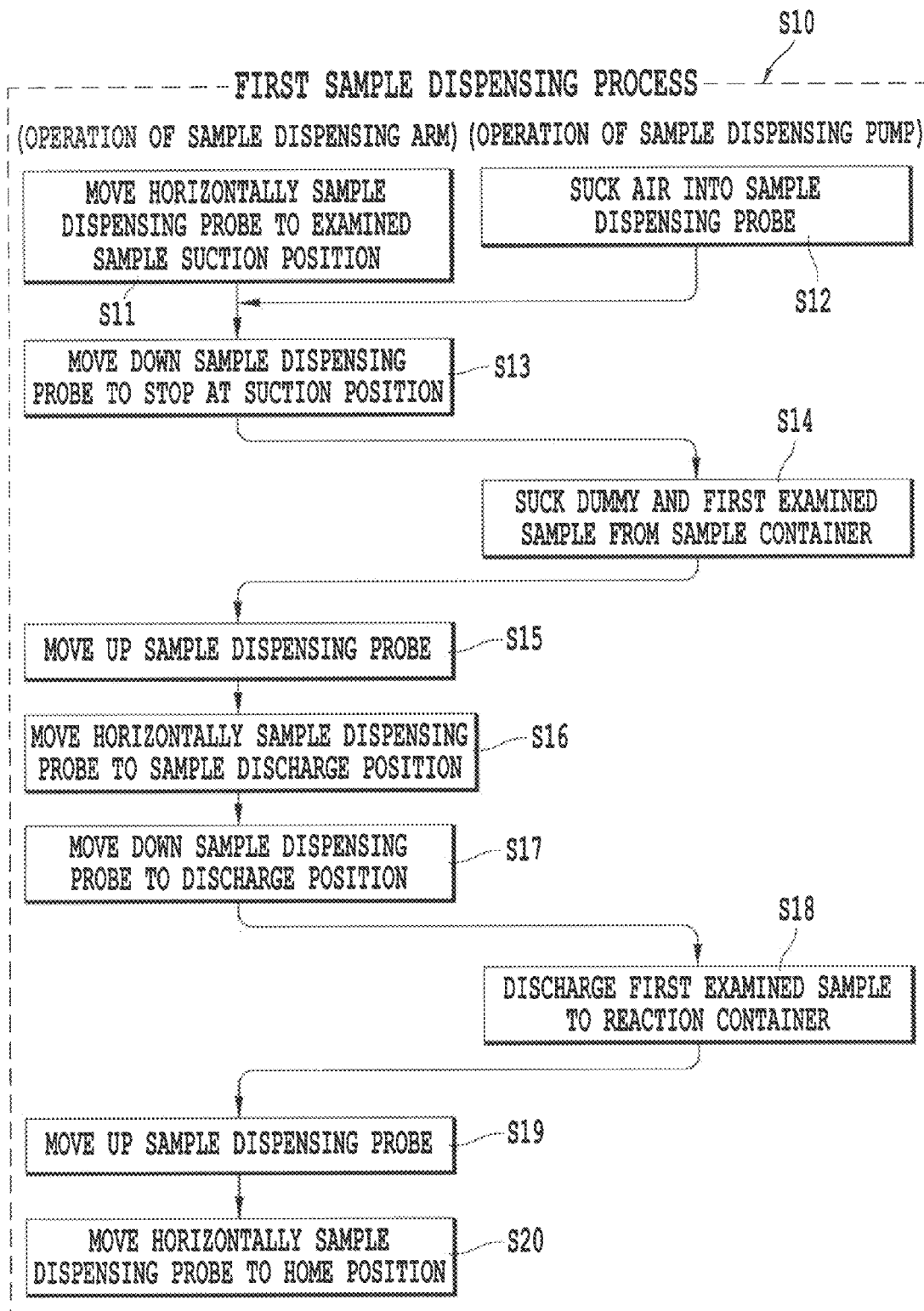
FIG. 5 is a flowchart showing a first sample dispensing process according to the embodiment of the invention.

FIG. 5 is a flowchart specifically showing the first sample dispensing process S10 shown in FIG. 4. The first sample dispensing process S10 includes Steps S11, S13, S15, S16, S17, S19, and S20 in accordance with an operation of the sample dispensing arm 10 and Steps S12, S14, and S18 in accordance with an operation of the sample dispensing pump 10a. In addition, FIGS. 7A, 7B, and 7C show a suction operation in which the sample dispensing pump 10a sucks the sample into the sample dispensing probe 16 in Steps S12 and S14.

First, the sample dispensing arm 10 rotates in a direction indicated by R2 shown in FIG. 3 so as to horizontally move the sample dispensing probe 16 from the sample dispensing probe cleaning position T4 corresponding to a home position to the examined sample suction position T2 (Step S11).

Figure 7A:
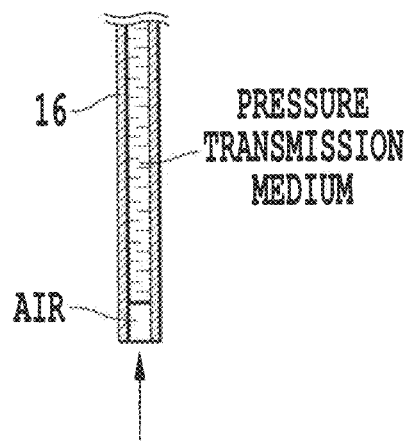
FIG. 7A is a view showing an air suction operation in a step of sucking an examined sample according to the embodiment of the invention.
Figure 7B:
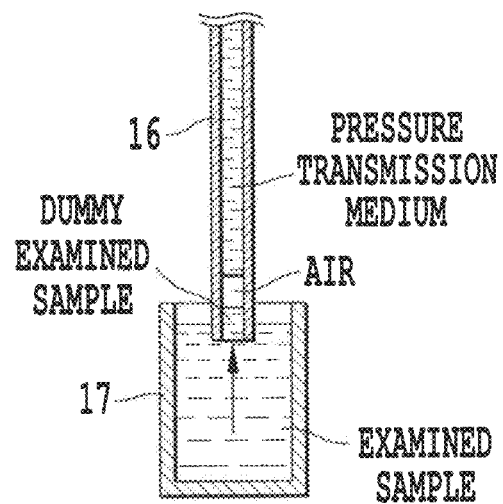
FIG. 7B is a view showing a dummy suction operation in a step of sucking the examined sample according to the embodiment of the invention.
Figure 7C:
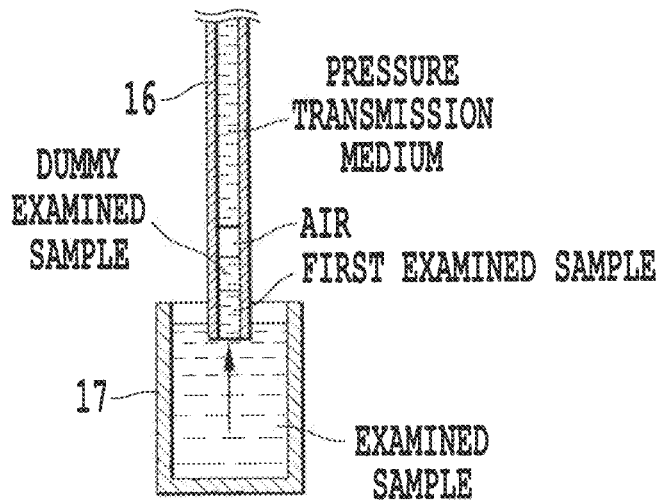
FIG. 7C is a view showing a first sample suction operation in a step of sucking the examined sample according to the embodiment of the invention.

In parallel with the horizontal movement of the sample dispensing probe 16, the sample dispensing pump 10a performs an air suction operation shown in FIG. 7A so as to suck air into the sample dispensing probe 16 (Step S12).

After air is sucked into the sample dispensing pump 10a, the sample dispensing arm 10 moves down the sample dispensing probe 16 toward the examined sample in the sample container 17 corresponding to an examined object stopped at a position below the examined sample suction position T2. Then, the sample dispensing arm allows the sample dispensing probe 16 to enter the examined sample at a first speed v1 so that the sample dispensing probe decelerates from a detection position (a first detection position) detected by the detector 18a and stops at a suction position (a first stop position) (Step S13).

In addition, in the following description, in fact, an acceleration/deceleration duration is included in a moving up/down operation of the sample dispensing probe 16. That is, when the sample dispensing probe 16 moves up/down, the probe is accelerated up to a predetermined speed. Subsequently, the sample dispensing probe moves at a constant speed at the time point when arriving at the predetermined speed and decelerates to stop. Here, for the convenient description, the description of the acceleration/deceleration will be omitted.

After the sample dispensing probe 16 moves down, the sample dispensing pump 10a performs a suction operation of the first examined sample in order to measure the examined sample. At this time, as shown in FIG. 7B, after the examined sample of a dummy not used for the measurement is sucked from the sample container 17 into the sample dispensing probe 16, as shown in FIG. 7C, the examined sample for the measurement is sucked in accordance with a predetermined sample amount in terms of a first dispensing operation (Step S14).

In addition, the examined sample is sucked into or discharged from the sample dispensing probe 16 via a pressure transmission medium inserted in a sealed state in a flow passage between the sample dispensing pump 10a and the sample dispensing probe 16. An air layer and an examined sample layer of a dummy not used for the measurement are provided between the first examined sample for the measurement sucked into the sample dispensing probe 16 and the pressure transmission medium. In terms of the air layer and the dummy layer, it is possible to prevent the examined sample for the measurement from diluting due to a mix with the pressure transmission medium.

After the suction operation of the first examined sample, the sample dispensing arm 10 moves up the sample dispensing probe 16 to the examined sample suction position T2 (Step S15).

After the sample dispensing probe moves up to the examined sample suction position T2, the sample dispensing arm 10 rotates in a direction indicated by R1 shown in FIG. 3 so as to horizontally move the sample dispensing probe 16 to the sample discharge position T1 (Step S16).

After the sample dispensing probe horizontally moves to the sample discharge position T1, the sample dispensing arm 10 moves down the sample dispensing probe 16 to the discharge position of the reaction container 4 stopped at the sample discharge position T1 (Step S17).

After the sample dispensing arm 10 moves down, the sample dispensing pump 10a discharges the first examined sample from the sample dispensing probe 16 to the reaction container 4 (Step S18).

After the discharge operation of the first examined sample, the sample dispensing arm 10 moves up the sample dispensing probe 16 to the sample discharge position T1 (Step S19).

After the sample dispensing probe moves up to the sample discharge position T1, the sample dispensing arm 10 rotates in a direction indicated by R2 so as to horizontally move the sample dispensing probe 16 to the home position (Step S20).

Figure 6:
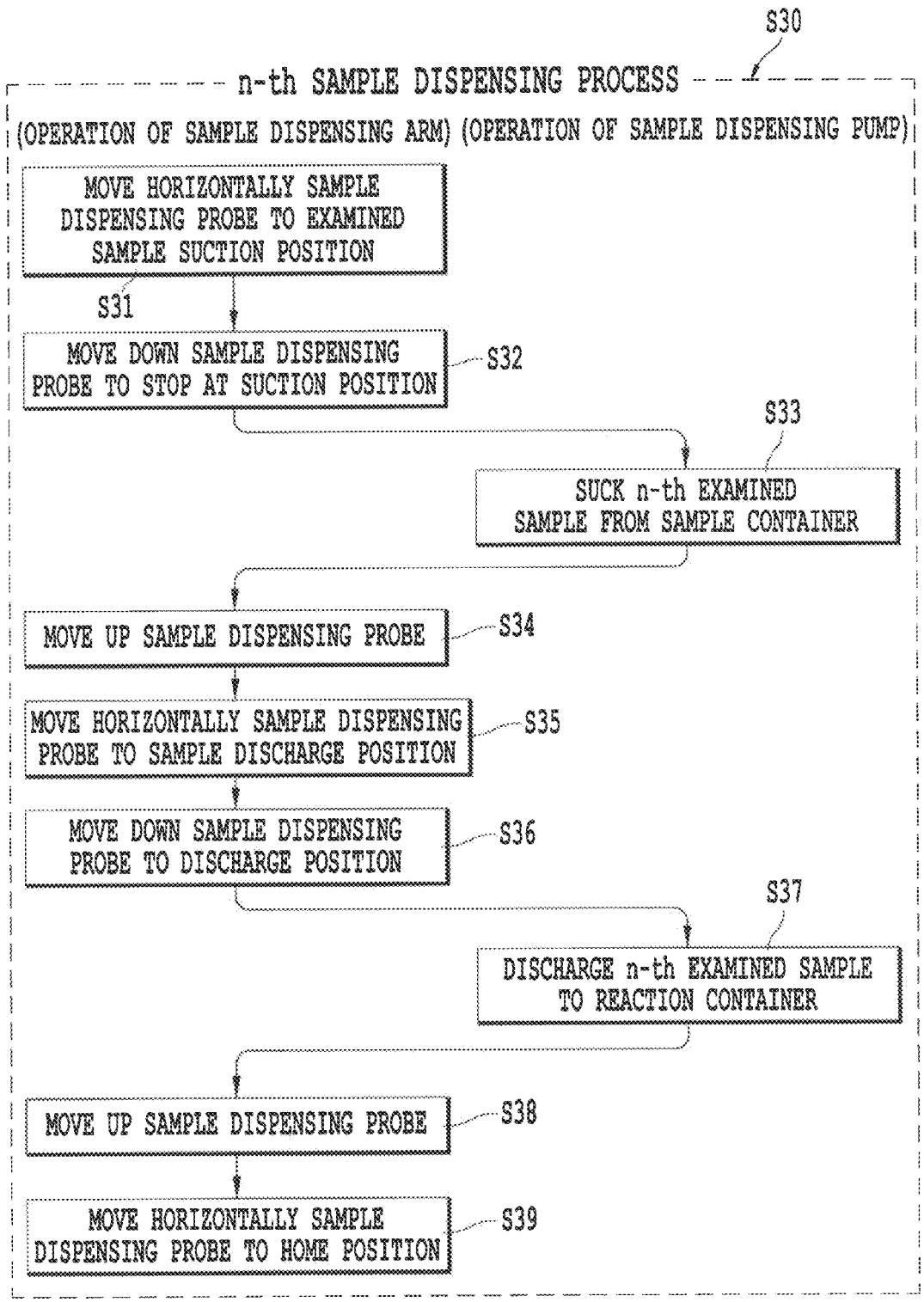
FIG. 6 is a flowchart showing an n-th sample dispensing process according to the embodiment of the invention.
Figure 7D:
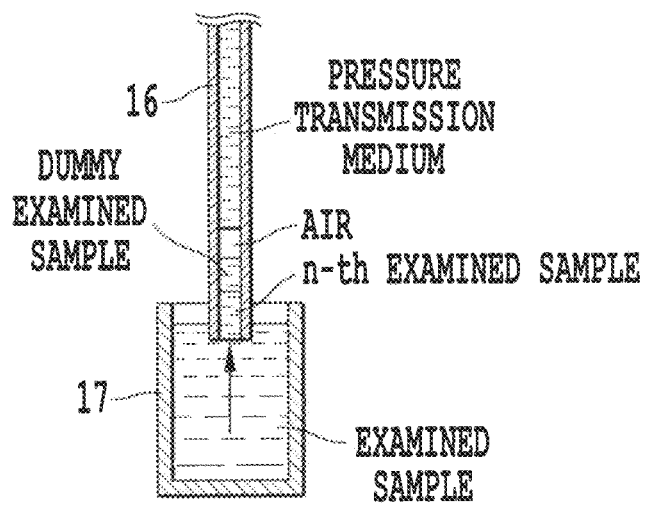
FIG. 7D is a view showing a second sample suction operation in a step of sucking the examined sample according to the embodiment of the invention.

FIG. 6 is a flowchart specifically showing the n-th sample dispensing process S30 shown in FIG. 4. The n-th sample dispensing process S30 includes Steps S31, S32, S34, S35, S36, S38, and S39 in accordance with an operation of the sample dispensing arm 10 and Steps S33 and S37 in accordance with an operation of the sample dispensing pump 10a. In addition, FIG. 7D shows the suction operation in which the sample is sucked into the sample dispensing probe 16 by the sample dispensing pump 10a in Step S33.

The sample dispensing arm 10 rotates in a direction indicated by R2 so as to horizontally move the sample dispensing probe 16 from the home position to the examined sample suction position T2 (Step S31).

After the sample dispensing probe 16 horizontally moves, the sample dispensing arm 10 moves down the sample dispensing probe 16. At this time, the sample dispensing probe 16 enters the same examined sample as the first examined sample at a second speed v2 slower than the first speed v1 so that the sample dispensing probe decelerates from a detection position (an n-th detection position) detected by the detector 18a and stops at a suction position (an n-th stop position) (Step S32).

After the sample dispensing probe 16 moves down, the sample dispensing pump 10a performs a suction operation of the same examined sample as the first examined sample at an n-th dispensing operation. At this time, as shown in FIG. 7D, in a state where the air and the examined sample of the dummy sucked at the first time are remained, the examined sample for the measurement in accordance with an n-th predetermined sample amount is sucked into the sampling dispensing probe 16 (Step S33).

After the suction operation of the n-th examined sample, the sample dispensing arm 10 moves up the sample dispensing probe 16 to the examined sample suction position T2 (Step S34).

After the sample dispensing probe moves up to the examined sample suction position T2, the sample dispensing arm 10 rotates in a direction indicated by R1 so as to horizontally move the sample dispensing probe 16 to the sample discharge position T1 (Step S35).

After the sample dispensing probe horizontally moves to the sample discharge position T1, the sample dispensing arm 10 moves down the sample dispensing probe 16 to the discharge position of the reaction container 4 stopped at the sample discharge position T1 (Step S36).

After the sample dispensing arm 10 moves down, the sample dispensing pump 10a discharges the n-th examined sample from the sample dispensing probe 16 to the reaction container 4 (Step S37).

After the discharge operation of the n-th examined sample, the sample dispensing arm 10 moves up the sample dispensing probe 16 to the sample discharge position T1 (Step S38).

After the sample dispensing probe moves up to the sample discharge position T1, the sample dispensing arm 10 rotates in a direction indicated by R2 so as to horizontally move the sample dispensing probe 16 to the home position (Step S39).

Then, as a next analysis cycle after dispensing the sample of the final measurement item of the same examined sample, in the cleaning pool provided at the sample dispensing probe cleaning position T4, a cleaning operation of the sample dispensing probe 16 is carried out after discharging the air and the examined sample of the dummy from the sample dispensing probe 16. After the cleaning operation, the sample dispensing probe 16 moves up to the home position and stays in a standby state for dispensing the next examined sample.

In this way, the n-th sample dispensing process S30 does not include the air suction operation in which air is sucked into the sample dispensing probe 16 in Step S12 and the suction operation in which the examined sample of the dummy is sucked into the sample dispensing probe 16 in Step S14 during the first sample dispensing process S10. Since the first sample dispensing process is set to 1 analysis cycle, it is possible to allocate the operation time of Steps S12 and S14 during the first sample dispensing process S10 to the operation time of Step S32 during the n-th sample dispensing process S30.

Figure 8:
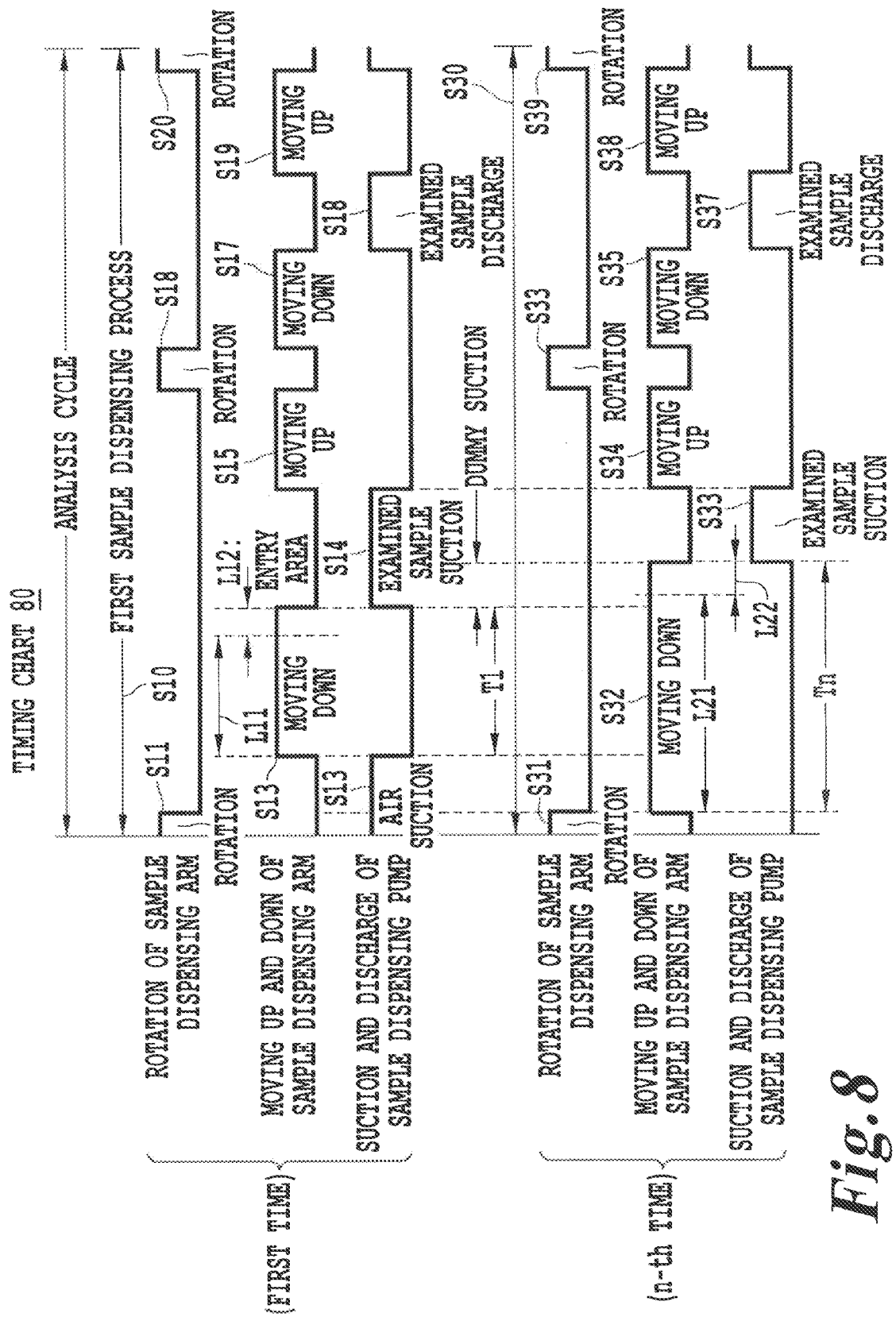
FIG. 8 is a timing chart showing a first sample dispensing process and an n-th sample dispensing process according to the embodiment of the invention.

FIG. 8 is a timing chart showing a timing for each step during the first and n-th sample dispensing processes S10 and S30 shown in FIGS. 5 and 6.

On the upper side of a timing chart 80, there are shown a suction/discharge operation timing of the sample dispensing pump 10a and a rotation/elevation operation timing of the sample dispensing arm 10 corresponding to Steps S11 to S20 during the first sample dispensing process S10. In addition, on the lower side thereof, there are shown a suction/discharge operation timing of the sample dispensing pump 10a and a rotation/elevation operation timing of the sample dispensing arm 10 corresponding to Steps S31 to S39 during the n-th sample dispensing process S30.

Then, when a maximum sample amount is set to the analysis condition for each measurement item, each operation timing is allocated so that the sample dispensing arm is disposed in the disk sampler 6 during 1 analysis cycle so as to suck a maximum sample amount of the examined sample from the sample container 17 in which the liquid surface of the examined sample is located at a minimum height capable of performing the suction operation and to again discharge the sucked maximum sample amount of the examined sample to the reaction container 4.

First, the operation timing of the sample dispensing arm 10 during the first and n-th sample dispensing processes S10 and S30 will be described. 'Rotation', 'moving down', and 'moving up' in Steps S11, S13, S15, S16, s17, S19, and S20 during the first sample dispensing process S10 and Steps S31, S32, S34, S35, S36, S38, and S39 during the n-th sample dispensing process S30 on the timing chart 80 indicate the rotation and elevation operations and the time of the sample dispensing arm 10.

In addition, in 'moving down' in Steps S13 and S32 and 'moving up' in Steps S15 and S34, a time necessary for moving up/down the sample dispensing arm between the examined sample suction position T2 and the suction position in the sample container 17 in which the liquid surface of the examined sample is set at a minimum height capable of performing the suction operation.

An operation start timing and an operation end timing of 'Horizontal movement' in Steps S11, S16, S20, S31, S35, and S39 of the first and n-th sample dispensing processes S10 and S30 do not change in every analysis cycle. In addition, an operation start timing of 'moving down' and 'moving up' in Steps S13, S15, S17, S19, S32, S34, S36, and S38 does not change in every analysis cycle, and an operation end timing changes depending on a height of the liquid surface of the examined sample in the sample container 17. That is, as the liquid surface of the examined sample is located at the lower position, it takes more time for performing the operations of 'moving down' and 'moving up', and thus an operation end timing becomes later.

Next, an operation timing of the sample dispensing pump 10a in the first and n-th sample dispensing processes S10 and S30 will be described. 'Air suction', 'examined sample suction', and 'examined sample discharge' in Steps S12, S14, and S18 during the first sample dispensing process S10 and Steps S33 and S37 during the n-th sample dispensing process S30 of the timing chart 80 respectively correspond to the air suction operation, the examined sample suction operation, the examined sample discharge operation, and the operation time of the sample dispensing pump 10a. The operation time has an allocated time necessary for sucking and discharging the maximum sample amount when the maximum sample amount is set to the analysis condition for each measurement item.

An operation start timing in each Steps and an operation end timing of 'air suction' in Step S12 during the first and n-th sample dispensing processes S10 and S30 do not change. An operation end timing in Steps S14, S18, S33, and S37 changes depending on the sample amount set for each measurement item. That is, as the set sample amount becomes larger, it takes more time to perform the operations of 'examined sample suction' and 'examined sample discharge', and thus an operation end timing becomes later.

Next, the operation timings of the same operations in Steps of the first and n-th sample dispensing processes S10 and S30 will be described by comparison.

The operations in Step S11 and Step S31 start at the same operation timing and have the same allocated operation time. The operations in Steps S15 to S20 start at the same operation timing of Steps S34 to S39 respectively and have the same allocated operation time.

The operation in Step S14 starts earlier than that of Step S33 by an amount sucking the examined sample of the dummy during 'examined sample suction', and they have the same allocated operation end timing.

Since Step S32, in which the sample dispensing probe 16 moves down from the examined sample suction position T2 to the suction position of the examined sample, does not have the operation of 'air suction' in Step S12, an operation start timing is earlier than that of Step S13, and an operation end timing is later than that of Step S13 by an unnecessary amount of sucking the dummy among the sucked examined sample in Step S14. Accordingly, in Step S32, it is possible to allow the sample dispensing probe 16 to enter the examined sample in the sample container 7 at the second speed v2 slower than the first speed v1.

Figure 9A:
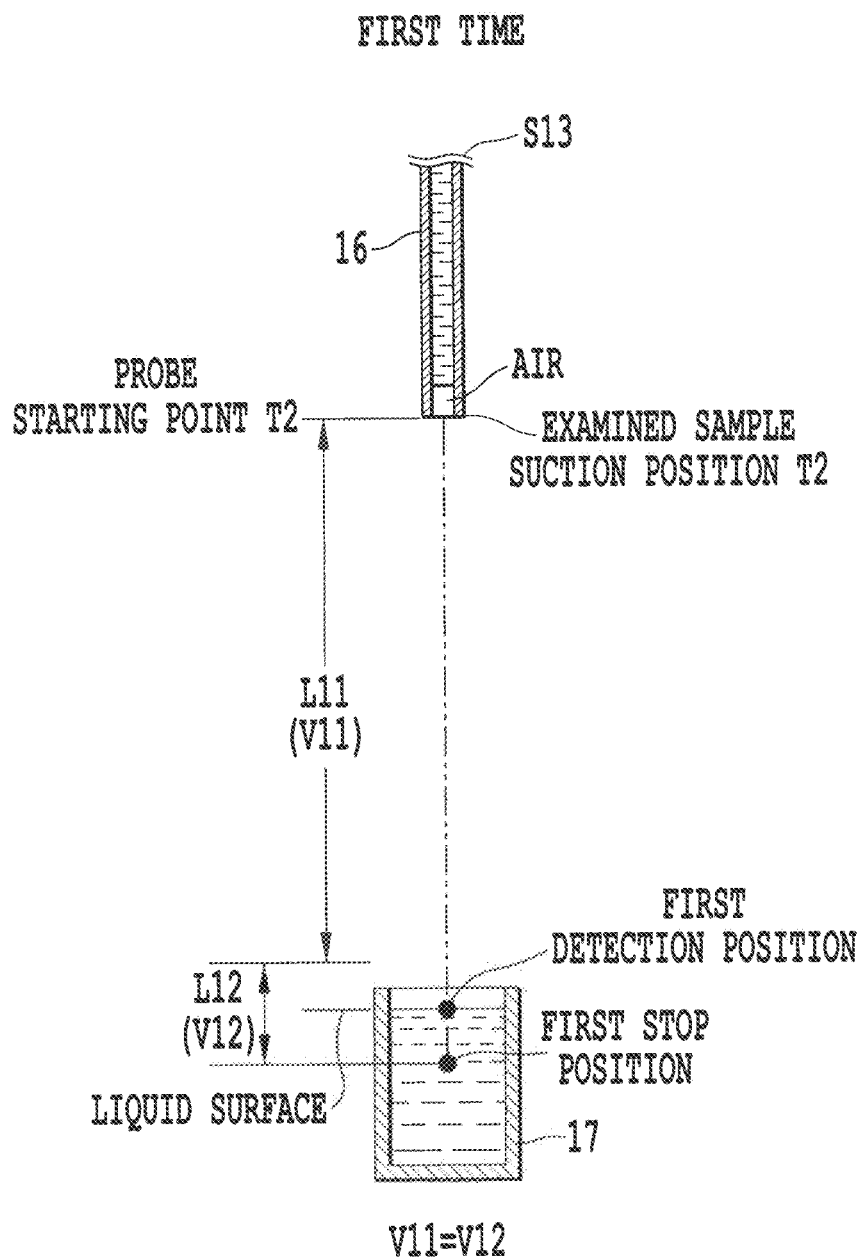
FIG. 9A is a view showing a first sample dispensing probe moving down operation for sucking the examined sample according to the embodiment of the invention.
Figure 9B:
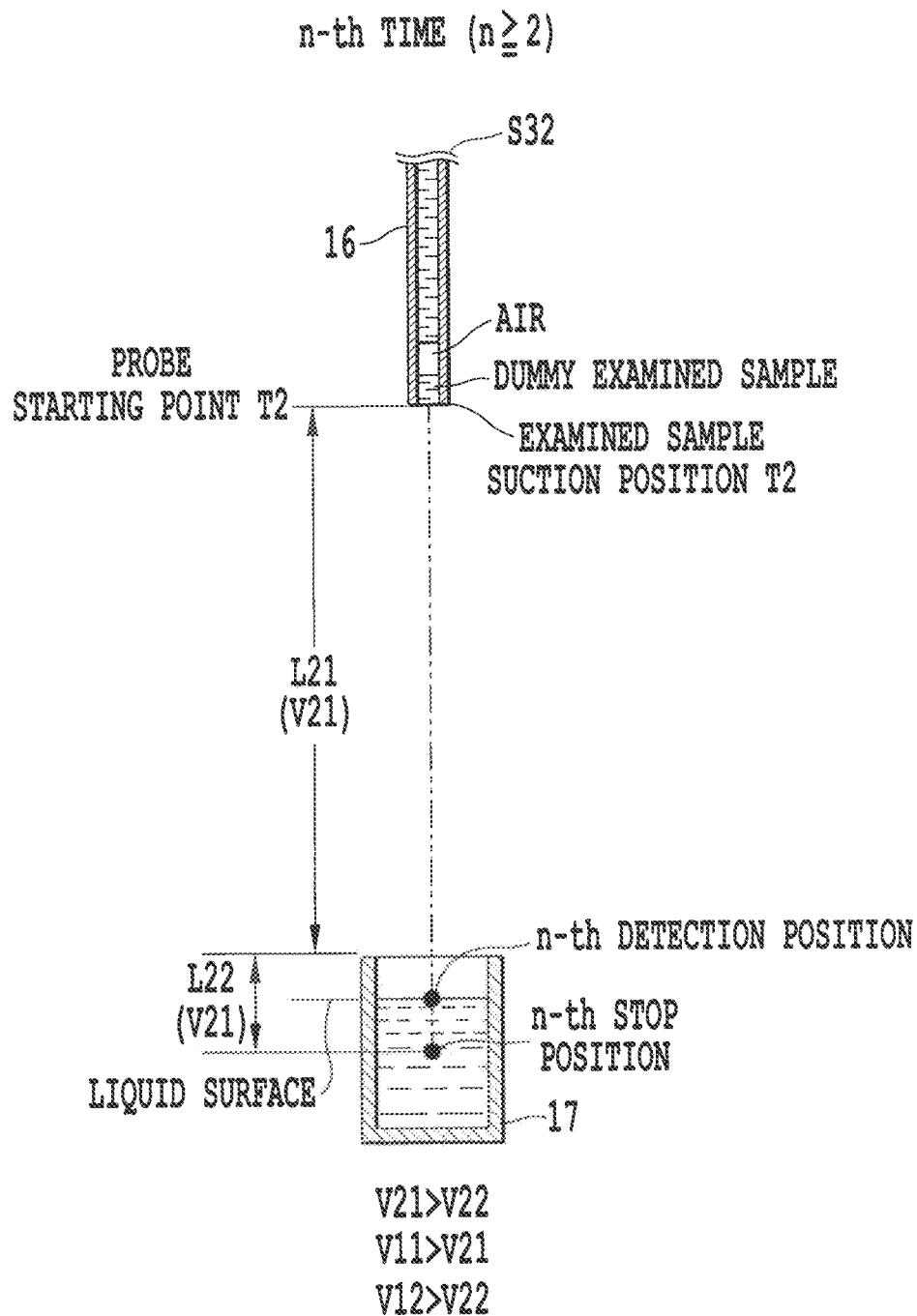
FIG. 9B is a view showing an n-th sample dispensing probe moving down operation for sucking the examined sample according to the embodiment of the invention.
Figure 10A:
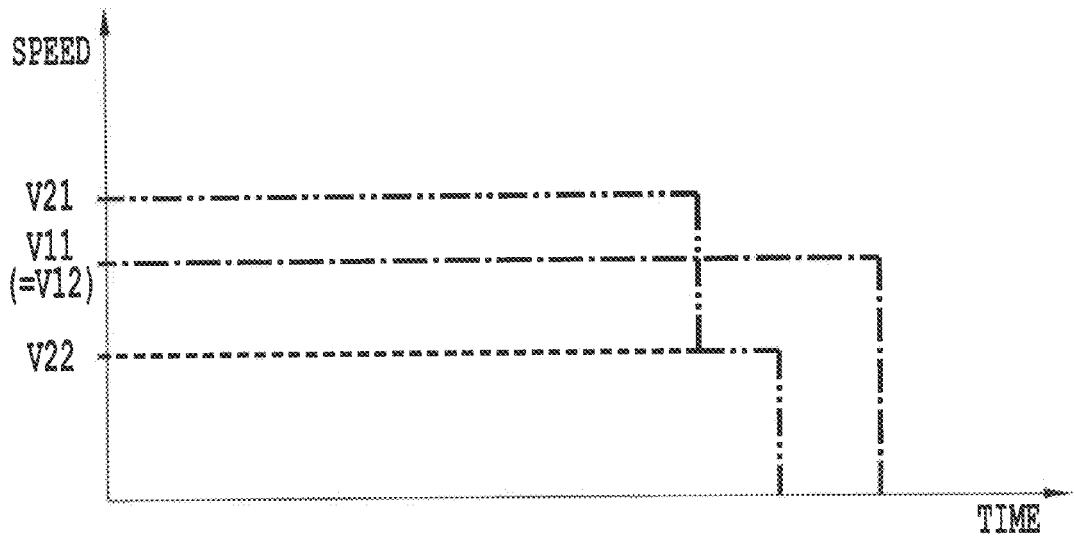
FIG. 10A is a view showing a speed sequence of the sample dispensing probe corresponding to FIGS. 9A and 9B.

FIGS. 9A and 9B are views showing an example of a moving down operation of the sample dispensing probe 16 in Steps S13 and S32. FIGS. 9A and 10A (dashed-dotted line) show a first operation of the sample dispensing probe 16 moving down from a probe start point (the highest position) T2 to the lowest point (a first stop position) in Step S13. As shown in FIG. 9A, the sample dispensing probe 16 moves down at a speed V11 in an area L11 before the entry. The sample dispensing probe 16 passes an area (an entry area) L12 having a predetermined distance before and after the liquid surface as the center while maintaining a speed V12 (V12=V11) and stops at the predetermined lowest position. The sample dispensing probe 16 enters the examined sample in the sample container 17 at a certain position in the entry area L12. The reason why the sample dispensing probe moves down at a constant speed from the area L11 before the entry to the entry area L12 is that a height of the liquid surface is not clear.

FIGS. 9B and 10A (dashed-two dotted line) show an operation from a second operation in which the sample dispensing probe 16 moves down from the probe start point T2 to the lowest point in Step S32. In addition, from the second operation, the control portion 32 recognizes the height of the liquid surface of the examined sample on the basis of a variation in output of a sensor mounted to the front end portion of the sample dispensing probe 16 during the first moving down operation. Accordingly, in the moving down operation of the sample dispensing probe 16 from the second operation, it is possible to distinguish the area L21 before the entry and the entry area L22.

As shown in FIG. 9B, the sample dispensing probe 16 moves down at a speed V21 in the area L21 before the entry. The speed V21 is set to be faster than a moving down speed V22 in the entry area L22. The speed V21 is set to be faster than the moving down speed V11 in the area L11 before the entry during the first moving down operation.

After the sample dispensing probe passes the area L21 before the entry at a high speed, in the entry area L22, the moving down speed V22 of the sample dispensing probe 16 becomes slower than the speed V21 in the area L21 before the entry. The moving down speed V22 becomes slower than the speed V12 in the entry area L12 at the first time. The sample dispensing probe 16 enters the examined sample in the sample container 17 at the substantially center position of the entry area L22 in a state where the slow moving down speed V22 is maintained.

Since the sample dispensing probe 16 enters the examined sample as slow as possible, it is possible to restrict a deterioration of dispensing precision of the examined sample and to reduce a contamination thereof.

As the n-th operation in Step S32, it is possible to ensure more time Tn necessary for the moving down operation of the sample dispensing probe 16 than the time T1 necessary for the first moving down operation of the sample dispensing probe as to be understood when the n-th sample dispensing process shown in FIG. 8 is compared with the first sample dispensing process. The reason is because the 'air-suction' and 'dummy-suction' necessary for the first operation is not necessary for the n-th operation.

As described above, the control portion 32 allows a speed at which the sample dispensing probe 16 enters the liquid surface of the examined sample for the n-th (n≥2) suction operation of the examined sample to be slower than a speed at which the sample dispensing probe 16 enters the liquid surface of the examined sample for the first suction operation of the examined sample. In the n-th suction operation, the control portion 32 controls the probe elevating mechanism in order to move down the sample dispensing probe 16 to the area L21 before the entry at the speed V21 faster than the entry speed V22 of the sample dispensing probe 16 in the area L22 having predetermined distance before and after the liquid surface of the examined sample as the center. In the first suction operation, the control portion 32 moves down the sample dispensing probe 16 at a constant speed. The control portion 32 moves down the sample dispensing probe 16 at a constant speed V11 (=V12) during the first suction operation and moves down at the speed V21 faster than the entry speed V22 of the sample dispensing probe 16 to the liquid surface of the examined sample and faster than the speed V11 during the n-th suction operation.

Figure 10B:
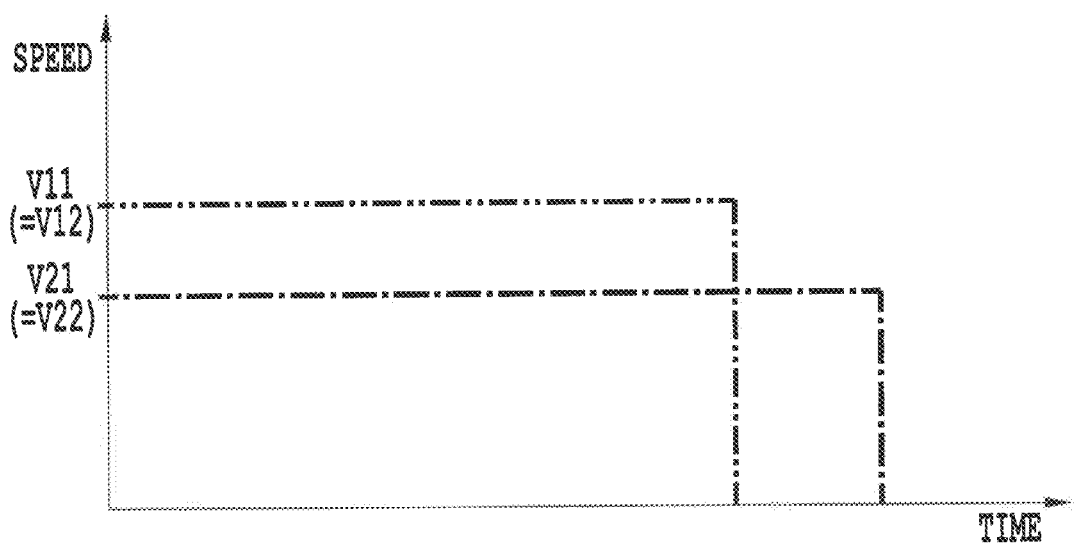
FIG. 10B is a view showing another speed sequence of the sample dispensing probe corresponding to FIGS. 9A and 9B.

As shown in FIG. 10B, the control portion 32 may move down the sample dispensing probe 16 at the constant speed V11 in the areas L11 and L12 during the first suction operation and may move down the sample dispensing probe 16 at the constant speed V21 (=V22) slower than the speed V11 in the areas L21 and L22 during the n-th suction operation.

In addition, the invention is not limited by the above-described embodiment, but the sample dispensing probe 16 may enter the examined sample in the sample container 17 at a third speed v3 slower than a second speed v2 during the n-th suction operation. The embodiment of this case will be described below.

In order to move down the sample dispensing probe 16 from the examined sample suction position T2 to an (n−1)-th detection position during the (n−1)-th suction operation, an internal storage circuit of the control portion 32 stores the number of driving pulses supplied to a driving mechanism, for example, a stepping motor of the sample dispensing arm 10. Then, on the basis of the stored number of driving pulses, the control portion 32 calculates the number of driving pulses necessary for moving down the sample dispensing probe 16 from the examined sample suction position T2 to an (n−1)a-th position above the (n−1)-th detection position and an (n−1) b-th position below the (n−1)a-th position and above the (n−1)-th detection position.

Then, on the basis of the number of driving pulses calculated during the (n−1)-th suction operation, the control portion moves down the sample dispensing probe 16 from the examined sample suction position T2 to the (n−1)a-th position at a fourth speed v4 faster than the first speed v1 during the n-th suction operation. Subsequently, after the sample dispensing probe decelerates from the (n−1)a-th position to the (n−1)b-th position, the sample dispensing probe 16 stops once or continuously moves down from the (n−1)b-th position to the examined sample in the sample container 17 at the third speed v3 slower than the second speed v2, due to the remaining time allocation in accordance with the moving down operation at the fourth speed v4. Subsequently, the sample dispensing probe decelerates from the n-th detection position detected by the detector 18a and stops at the n-th stop position. Accordingly, since the sample dispensing probe can enter the examined sample at the third speed v3 slower than the second speed v2, it is possible to more reduce a shock generated upon stopping at the stop position than that at the second speed v2.

In this way, in the n-th suction operation of the examined sample, since the sample dispensing probe 16 can enter the examined sample in the sample container 17 at the second speed v2 or the third speed v3 slower than the first speed v1 at the first suction operation, it is possible to more reduce a shock generated upon stopping at the suction position than that of the first suction operation. Accordingly, it is possible to reduce a case where the air layer formed inside the sample dispensing probe 16 during the first suction operation is thinned by the dispensing operations from the second dispensing operation and to reduce a case where the dummy examined sample sucked during the first suction operation dilutes in terms of the reduction. Also, it is possible to dispense the examined sample from the second dispensing operation with high precision upon dispensing the same examined sample a plurality of times.

According to an experiment result of an actual operation, it is possible to reduce a case where the examined sample having been dispensed in the former dispensing operation enters the sample container 17 having the next examined sample via the sample dispensing probe 16.

Figure 11:
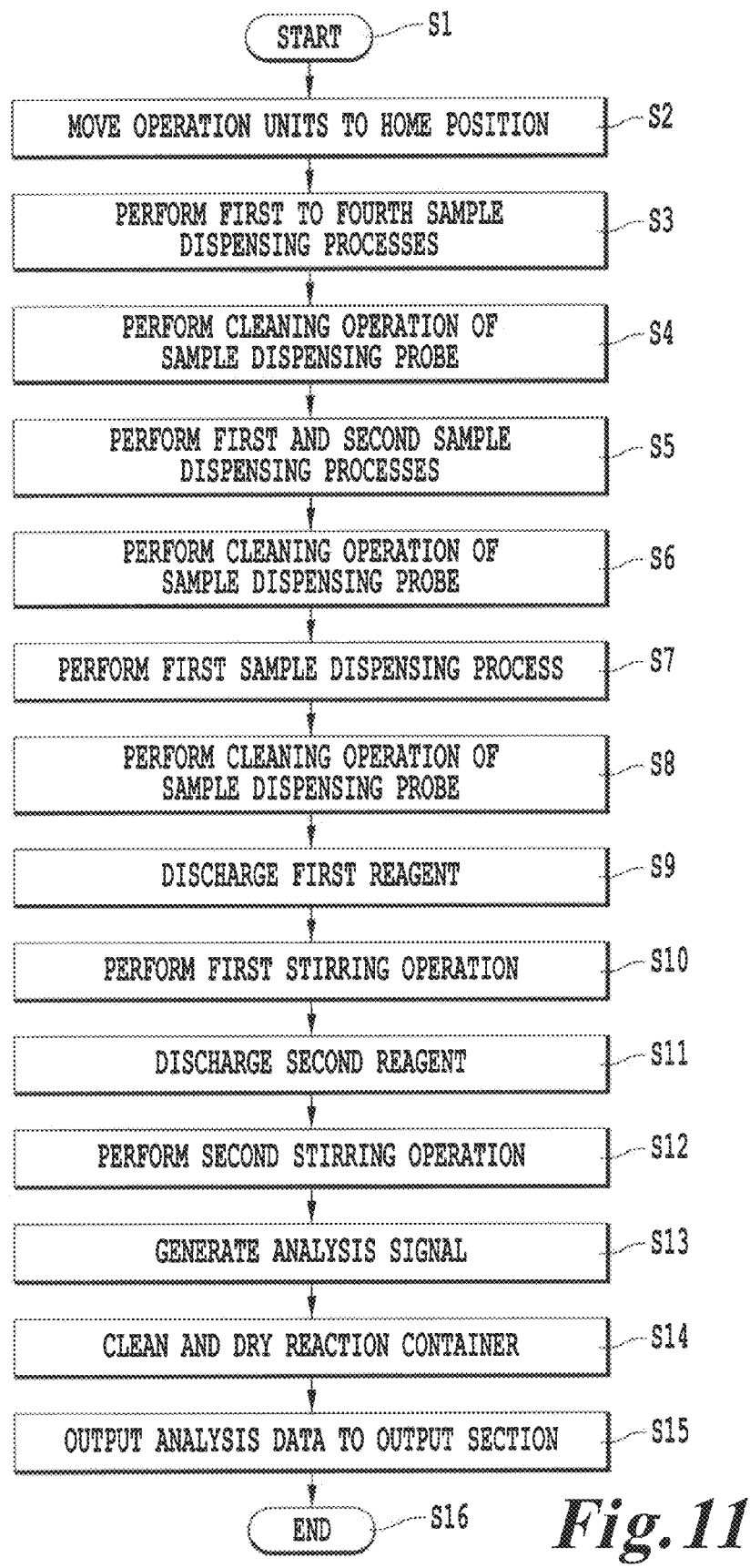
FIG. 11 is a flowchart showing an operation of the autoanalyzer according to the embodiment of the invention.
Figure 12:
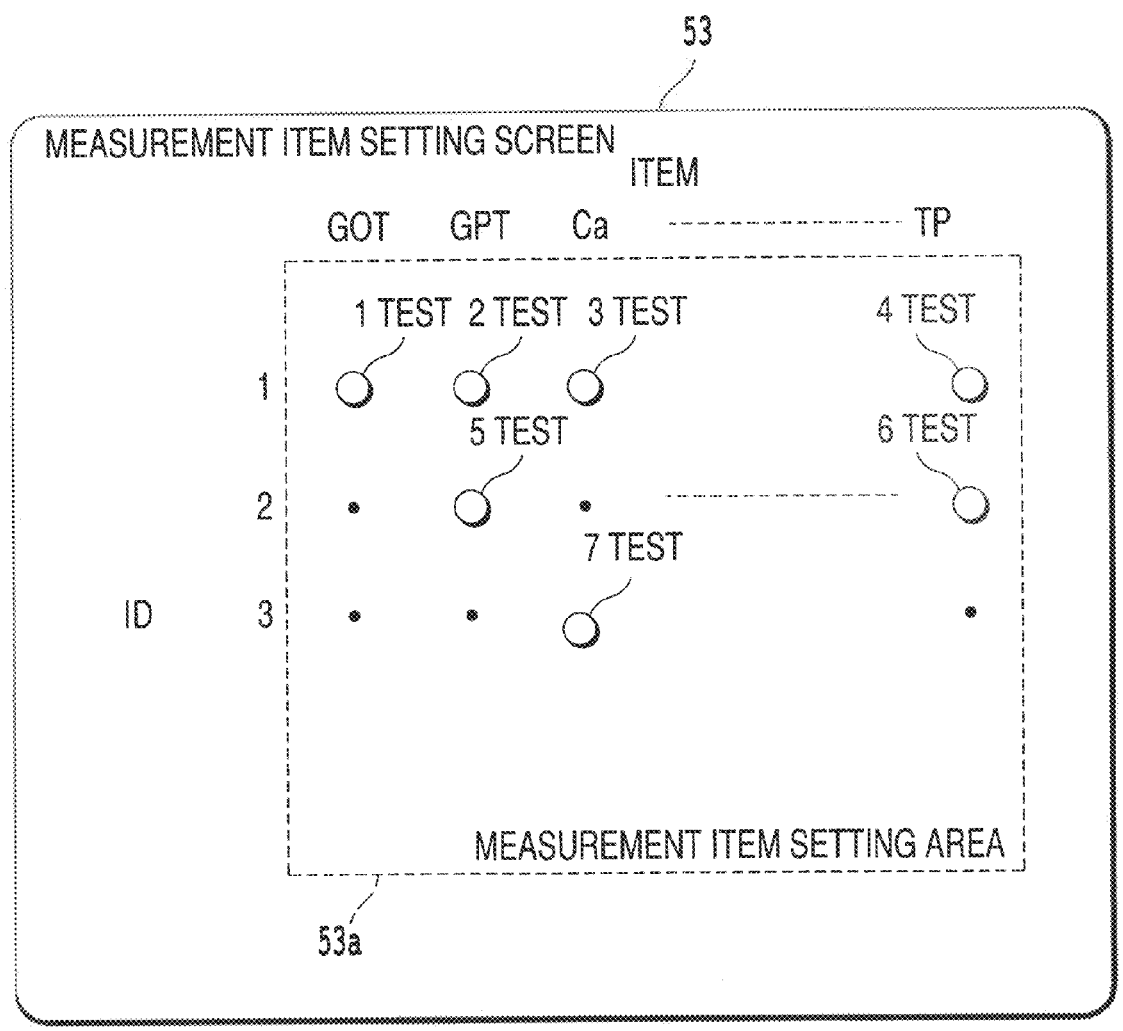
FIG. 12 is a view showing an example of a measurement item setting screen according to the embodiment of the invention.
Figure 13:
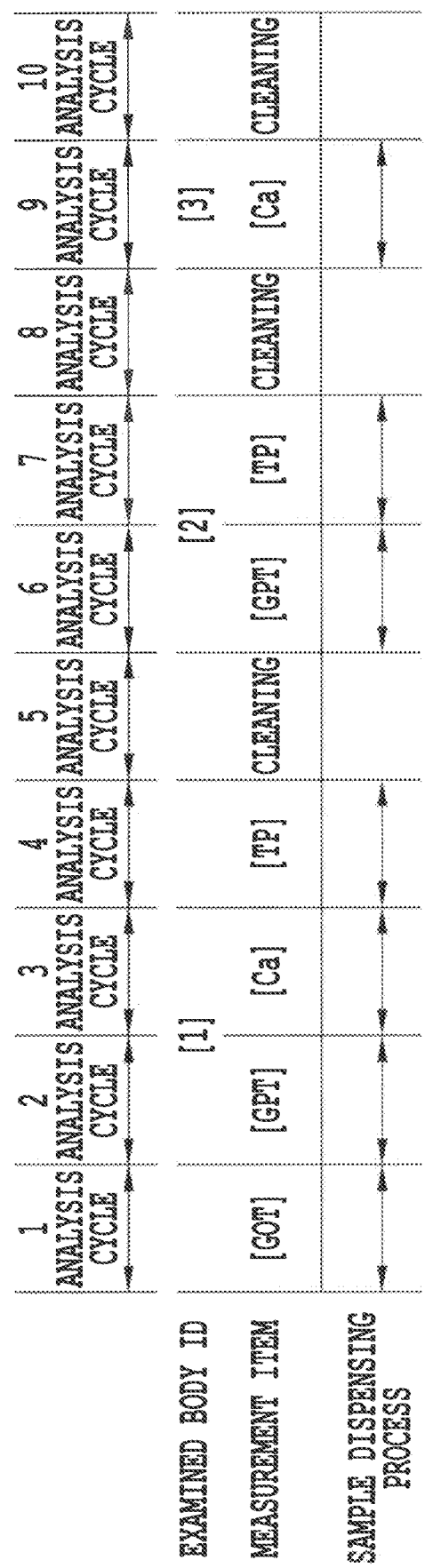
FIG. 13 is a view showing a sample dispensing process corresponding to each measurement item for each examined sample selectively input from the measurement item setting screen according to the embodiment of the invention.

Next, an operation of the autoanalyzer 100 will be described with reference to FIGS. 1 to 13. FIG. 11 is a flowchart showing an example of an operation of the autoanalyzer 100. FIG. 12 shows an example of the measurement item setting screen displayed in the display portion 52. FIG. 13 shows the sample dispensing process corresponding to each measurement item for each examined sample selectively input from the measurement item setting screen.

In terms of a calibration operation from the operation section 60, the storage portion 42 of the analysis data process section 40 stores the calibration table for each measurement item in advance. In addition, in terms of the selective input of the measurement item from the operation section 60, the internal storage circuit of the system control section 70 stores the measurement item selectively input for each examined sample.

FIG. 12 is a view showing an example of the measurement item setting screen selectively input and displayed in the display portion 52. The measurement item setting screen 53 includes a section of 'ID' for displaying an ID of the examined body input to the examined body information input screen, a section of 'item' for displaying an item name in abbreviation, and a measurement item setting area 53a for setting a measurement item of the item name displayed in the section of 'item' for each ID of the examined body displayed in the section of 'ID'.

In the section of 'ID', for example, the IDs '1' to '3' of the examined body are input in advance and are displayed. In addition, in the section of 'item', for example, the item names 'GOT', 'GPT', 'Ca', 'TP', and the like are displayed.

In the measurement item setting area 53a, when the item name is set in the section of 'item' corresponding to the ID of each examined body in the section of 'ID', 'O' is displayed, and when the item name is not set, '.' is displayed. Then, for example, when the operation section 60 sets 'GOT', 'GPT', 'Ca', and 'TP' with respect to '1' displayed in the section of 'ID', 'O' is displayed in sections of '1 test' to '4 test' of the measurement item setting area 53a.

In addition, when the operation section sets 'GPT' and 'TP' with respect to '2' displayed in the section of 'ID', 'O' is displayed in sections of '5 test' and '6 test' of the measurement item setting area 53a, and when the operation section sets 'Ca' with respect to '3' displayed in the section of 'ID', 'O' is displayed in a section of '7 test' of the measurement item setting area 53a.

The measurement item setting information set and input from the measurement item setting screen 53 is stored in the internal storage circuit of the system control section 70. Then, the measurement of the examined sample is carried out on the basis of the measurement item information selectively input from the measurement item setting screen 53, and the measurement is carried out in an order of the examined sample from the one corresponding to '1' on the uppermost 'ID' and in an order of the measurement item from 'GOT' set on the left side of the ID of each examined body.

First, in terms of a measurement start operation from the operation section 60, the autoanalyzer 100 starts the operation (Step S1 shown in FIG. 11).

The system control section 70 commands the analysis control section 30, the analysis data process section 40, and the output section 50 to measure the measurement item for each examined sample stored in the internal storage circuit. The control portion 32 of the analysis control section 30 first moves the analysis units of the analysis section 19 to the home position and starts the measurement operation (Step S2 shown in FIG. 11).

As shown in FIG. 13, the analysis section 19 having started the measurement operation performs the first sample dispensing process S10 for dispensing the examined sample for measuring 'GOT' of the examined body ID '1' selectively input from the measurement item setting screen 53 in 1 analysis cycle. In addition, the analysis section performs the second to fourth sample dispensing processes S30 for measuring 'GPT', 'Ca', and 'TP' in 2 to 4 analysis cycles (Step S3 shown in FIG. 11).

In the first sample dispensing process S10, the sample dispensing arm 10 rotates in a direction indicated by R1 so as to horizontally moves the sample dispensing probe 16 from the sample dispensing probe cleaning position T4 to the examined sample suction position T2 where the sample container 17 having the examined sample of the examined body ID '1' is stopped. In parallel with the horizontal movement of the sample dispensing probe 16, the sample dispensing pump 10a sucks air within the sample dispensing probe 16.

After the air suction operation of the sample dispensing pump 10a, the sample dispensing arm 10 moves down the sample dispensing probe 16 at the examined sample suction position T2 and allows the sample dispensing probe to enter the examined sample at the first speed v1. Subsequently, the sample dispensing arm allows the sample dispensing probe to decelerate from the first detection position detected by the detector 18a to stop at the first stop position.

After the sample dispensing probe 16 moves down, the sample dispensing pump 10a sucks the dummy examined sample and the examined sample of 'GOT' ('1 test' shown in FIG. 12) from the sample container 17 into the sample dispensing probe 16.

After the examined sample suction operation of the sample dispensing pump 10a, the sample dispensing arm 10 moves up, rotates in a direction indicated by R2, and then moves down so that the sample dispensing probe 16 moves to the discharge position of the reaction container 4 stopped at the sample discharge position T1.

After the sample dispensing arm 10 moves down, the sample dispensing pump 10a discharges the examined sample of 'GOT' from the sample dispensing probe 16 to the reaction container 4.

After the examined sample discharge operation of the sample dispensing pump 10a, the sample dispensing arm 10 moves up and rotates in a direction indicated by R1 so that the sample dispensing probe 16 moves to the sample dispensing probe cleaning position T4.

The second sample dispensing process S30 for dispensing the examined sample of 'GPT' of the examined body ID '1' is continuously carried out from the first sample dispensing process S10.

The sample dispensing arm 10 rotates in a direction indicated by R1 so as to horizontally move the sample dispensing probe 16 from the sample dispensing probe cleaning position T4 to the examined sample suction position T2 of the sample container 17 having the examined sample, and moves down again so as to allow the sample dispensing probe to enter the examined sample of the examined sample ID '1' at the second speed v2. Subsequently, the sample dispensing arm allows the sample dispensing probe to decelerate from the second detection position detected by the detector 18a and to stop at the second stop position.

After the sample dispensing probe 16 moves down, the sample dispensing pump 10a sucks the examined sample of 'GPT' ('2 test' shown in FIG. 12) within the sample dispensing probe 16.

After the examined sample suction operation of the sample dispensing pump 10a, the sample dispensing arm 10 moves up, rotates in a direction indicated by R2, and then moves down so that the sample dispensing probe 16 moves to the discharge position of the reaction container 4 stopped at the sample discharge position T1.

After the sample dispensing arm 10 moves down, the sample dispensing pump 10a performs the suction operation, and discharges the examined sample of 'GPT' from the sample dispensing probe 16 to the reaction container 4.

After the examined sample discharge operation of the sample dispensing pump 10a, the sample dispensing arm 10 moves up and rotates in a direction indicated by R1 so that the sample dispensing probe 16 moves to the sample dispensing probe cleaning position T4.

Next, in 3 and 4 analysis cycles shown in FIG. 13, the analysis section 19 performs the third and fourth sample dispensing processes S30 for dispensing the examined sample of 'Ca' and 'TP' of each examined body ID '1' in the same way as the operation in 2 analysis cycle.

Next, in 5 analysis cycle shown in FIG. 13, after the dummy examined sample of the examined body ID '1' and air within the sample dispensing probe 16 is discharged, the analysis section 19 performs the sample dispensing probe cleaning operation for cleaning the examined sample attached to the sample dispensing probe 16 (Step S4 shown in FIG. 11).

That is, the sample dispensing arm 10 moves down and stops until the front end portion of the sample dispensing probe 16 arrives at a cleaning liquid discharge port of the cleaning pool provided in the sample dispensing probe cleaning position.

After the sample dispensing arm 10 moves down, the sample dispensing pump 10a cleans an inner wall of the sample dispensing probe 16. In addition, an outer wall of the sample dispensing probe 16 is cleaned by the cleaning liquid from the cleaning liquid discharge port in the cleaning pool.

After the sample dispensing probe 16 is cleaned, in 6 analysis cycle shown in FIG. 13, the analysis section 19 performs the first sample dispensing process S10 for dispensing the examined sample for measuring 'GPT' of the examined body ID '2'. In 7 analysis cycle shown in FIG. 13, the analysis section performs the second sample dispensing process S30 for dispensing the examined sample for measuring 'TP' of the examined body ID '2' (Step S5 shown in FIG. 11).

Then, in 8 analysis cycle shown in FIG. 13, after the dummy examined sample of the examined body ID '2' and air within the sample dispensing probe 16 are discharged, the analysis section 19 performs a sample dispensing probe cleaning operation for cleaning the examined sample of the examined body ID '2' attached to the sample dispensing probe 16 (Step S6 shown in FIG. 11).

Next, in 9 analysis cycle shown in FIG. 13, the analysis section 19 performs the first sample dispensing process S10 for dispensing the examined sample for measuring 'Ca' of the examined body ID '3' (Step S7 shown in FIG. 11).

Then, in 10 analysis cycle shown in FIG. 13, after the dummy examined sample of the examined body ID '3' and air within the sample dispensing probe 16 are discharged, the analysis section 19 performs the sample dispensing probe cleaning operation for cleaning the examined sample of the examined body ID '3' attached to the sample dispensing probe 16 (Step S8 shown in FIG. 11).

After the examined samples of the examined body IDs '1' to '3' are dispensed and the sample dispensing probe cleaning operation is performed by repeating such operations, when the reaction container 4, to which the examined samples of the examined body IDs '1' to '3' are dispensed, stops at the first reagent discharge position, the first reagent corresponding to the measurement item of each reaction container 4 is discharged from the first reagent dispensing probe 14 (Step S9 shown in FIG. 11).

After the first reagent is discharged, when the reaction container 4, to which the mixed liquid of the first reagent and the examined samples of the examined body IDs '1' to '3' is inserted, stops at the first stirring position, the mixed liquid within the reaction container 4 is stirred by the first stirrer of the first stirring unit 11a (Step S10 shown in FIG. 11).

After the first stirring operation, when the reaction container 4, to which the mixed liquid of the first reagent and the examined samples of the examined body IDs '1' to '3' is inserted, stops at the second reagent discharge position, the second reagent corresponding to the second reagent measurement item of 'GOT', 'GPT', and 'Ca' is discharged from the second reagent dispensing probe 15 into each reaction container 4 (Step S11 shown in FIG. 11).

After the second reagent is discharged, when the reaction container 4, to which the mixed liquid of the first reagent, the second reagent, and the examined samples of the examined body IDs '1' to '3' is inserted, stops at the second stirring position, the mixed liquid within the reaction container 4 is stirred by the second stirrer of the second stirring unit 11b (Step S12 shown in FIG. 11).

After the second stirring operation, when the reaction container 4, to which the mixed liquid of the examined sample, the first reagent and the second reagent and the mixed liquid of the examined sample and the first reagent are inserted, passes the photometric position, the photometric unit 13 irradiates light to the reaction container 4 and measures the light absorption degree of the set wavelength on the basis of the transmitted light. Then, the photometric unit generates the analysis signal for each measurement item of the examined samples of the examined body IDs '1' to '3' and outputs the analysis signal to the analysis data process section 40 (Step S13 shown in FIG. 11).

After the measurement, when the reaction container 4, to which the mixed liquid of the examined samples of the examined body IDs '1' to '3' is inserted, stops at the cleaning and drying position, the cleaning unit 12 sucks the mixed liquid within the reaction container 4 having passed the measurement and cleans and dries the inside of the reaction container 4 (Step S14 shown in FIG. 11).

The calculation portion 41 of the analysis data process section 40 generates the analysis data of each measurement item for each examined sample on the basis of the analysis signal output from the photometric unit 13, stores the analysis data in the storage portion 42, and then outputs the analysis data to the output section 50 (Step S15 shown in FIG. 11).

Then, after the cleaning and drying operation of all reaction containers 4 ends, the autoanalyzer 100 ends the measurement operation at the time point when the analysis data of all measurement items of the examined body IDs '1' to '3' is output (Step S16 shown in FIG. 11).

According to the above-described embodiments of the invention, in a case where the same examined sample is dispensed a plurality of times, since an unnecessary operation time from the second dispensing operation in the operation time of the first dispensing operation is allocated to the operation time for moving down the sample dispensing probe 16 from the upside of the sample container 17 to suck the examined sample, it is possible to allow the sample dispensing probe 16 to enter the examined sample in the sample container 17 during the suction operation from the second dispensing operation at a speed slower than that of the first dispensing operation. Accordingly, it is possible to improve precision in dispensing the examined sample after the second dispensing operation upon dispensing the same examined sample a plurality of times and to measure the examined sample with high precision.

The invention is not limited to the above-described embodiments, but may be modified in various forms without departing from the spirit and scope of the invention. Various inventions may be formed in an appropriate combination with a plurality of constituents shown in the above-described embodiments. For example, some constituents may be omitted from all constituents shown in the above-described embodiments. Then, the constituents shown in different embodiments may be appropriately used in a combination.

The invention is applied to an autoanalyzer and a method of elevating a probe for dispensing an examined sample with high precision.

What is claimed is:

1. An autoanalyzer comprising:
a measurement unit which measures a reaction liquid produced by an interaction between a reagent and an examined sample accommodated in a reaction container;
a sample probe which sucks the examined sample from a sample container and discharges the examined sample to the reaction container;
a probe elevating mechanism which elevates the sample probe with respect to the sample container;
a liquid surface detector which detects a liquid surface of the examined sample;
a storage which stores a level of the liquid surface of the examined sample detected by the liquid surface detector, during a first suction operation of the examined sample; and
a control unit which controls the probe elevating mechanism based on the level of the liquid surface of the examined sample stored in the storage to control a speed of lowering the probe in a pre-entering period prior to the probe entering the liquid surface and an entering period when the probe enters the liquid surface, and wherein during a first suction operation the probe is lowered at a first speed during both the pre-entering period and the entering period, and in a second suction operation of the examined sample, performed after the first suction operation, the probe is lowered at a second speed greater than the first speed in the pre-entering period and is lowered at a third speed less than the first speed during the entering period, and so that an entering speed of the sample probe at which the sample probe enters the liquid surface of the examined liquid in the second suction operation performed after the first suction operation is slower than an entering speed of the sample probe at which the sample probe enters the liquid surface of the examined sample in the first suction operation.

2. An autoanalyzer probe elevating method for elevating a sample probe to suck an examined sample from a sample container,
the method comprising:
detecting a liquid surface of the examined sample;
storing a level of the detected liquid surface of the examined sample; and
performing control based on the stored level of the liquid surface of the examined sample, to control a speed of lowering the probe in a pre-entering period prior to the probe entering the liquid surface and an entering period when the probe enters the liquid surface, and wherein during a first suction operation the probe is lowered at a first speed during both the pre-entering period and the entering period, and in a second suction operation of the examined sample, which is performed after a first suction operation, the probe is lowered at a second speed greater than the first speed in the pre-entering period and is lowered at a third speed less than the first speed during the entering period, and so that an entering speed of the sample probe at which the sample probe enters the liquid surface of the examined liquid in the second suction operation performed after the first suction operation is slower than an entering speed of the sample probe at which the sample probe enters the liquid surface of the examined sample in the first suction operation.

3. An autoanalyzer comprising:
a measurement unit which measures a reaction liquid produced by an interaction between a reagent and an examined sample accommodated in a reaction container;
a sample probe which sucks the examined sample from a sample container and discharges the examined sample to the reaction container;
a probe elevating mechanism which elevates the sample probe with respect to the sample container;
a suction controller which controls the sample probe such that at least one of air and a dummy examined sample not used for measurement is sucked before a first suction operation of the examined sample; and
a control unit to control a speed of lowering the probe in a pre-entering period prior to the probe entering a liquid surface and an entering period when the probe enters the liquid surface, and wherein during a first suction operation the probe is lowered at a first speed during both the pre-entering period and the entering period, and in a second and subsequent suction operations performed after the first suction operation, the probe is lowered at a second speed greater than the first speed in the pre-entering period and is lowered at a third speed less than the first speed during the entering period so that a speed at which the sample probe enters a liquid surface of the examined sample to perform an n-th suction operation of the examined sample ($n \geq 2$) is slower than a speed at which the sample probe enters the liquid surface of the examined sample to perform the first suction operation of the examined sample.

4. The autoanalyzer according to claim 3, wherein the control unit controls the probe elevating mechanism so that the sample probe moves down at a first speed during the first suction operation and the sample probe moves down at a second speed slower than the first speed during the n-th suction operation.

5. A probe elevating method which an autoanalyzer uses for elevating a sample probe in order to suck an examined sample from a sample container, the method comprising:

sucking either air or a dummy examined sample not used for measurement before a first suction operation of the examined sample; and controlling a speed of lowering the probe in a pre-entering period prior to the probe entering a liquid surface and an entering period when the probe enters the liquid surface, and wherein during a first suction operation the probe is lowered at a first speed during both the pre-entering period and the entering period, and in a second and subsequent suction operation, performed after the first suction operation, the probe is lowered at a second speed greater than the first speed in the pre-entering period and is lowered at a third speed less than the first speed during the entering period, so that a speed at which the sample probe enters a liquid surface of the examined sample to perform an n-th suction operation of the examined sample (n≥2) is slower than a speed at which the sample probe enters the liquid surface of the examined sample to perform the first suction operation of the examined sample.

* * * * *